(12) United States Patent
Gordon et al.

(10) Patent No.: US 7,744,573 B2
(45) Date of Patent: Jun. 29, 2010

(54) CLOSED BLOOD SAMPLING SYSTEM WITH ISOLATED PRESSURE MONITORING

(75) Inventors: Mark Gordon, San Clemente, CA (US); John Liu, Corona, CA (US); Scott Couchman, Irvine, CA (US); Hagay Drori, Rosh-Pina (IL)

(73) Assignee: Edwards Lifesciences Corporation, Irvine, CA (US)

( * ) Notice: Subject to any disclaimer, the term of this patent is extended or adjusted under 35 U.S.C. 154(b) by 657 days.

(21) Appl. No.: 11/521,610

(22) Filed: Sep. 13, 2006

(65) Prior Publication Data

US 2007/0179407 A1 Aug. 2, 2007

Related U.S. Application Data

(60) Provisional application No. 60/717,119, filed on Sep. 13, 2005, provisional application No. 60/720,263, filed on Sep. 21, 2005.

(51) Int. Cl.
*A61M 5/00* (2006.01)
*A61M 1/00* (2006.01)
*B65D 81/00* (2006.01)

(52) U.S. Cl. .......................... 604/248; 604/32; 600/584

(58) Field of Classification Search ................. 137/555, 137/556, 556.6; 600/573, 576, 578, 579, 600/581, 584; 604/32, 248, 401
See application file for complete search history.

(56) References Cited

U.S. PATENT DOCUMENTS

| | | | |
|---|---|---|---|
| 1,633,074 A | 6/1927 | De Mott | |
| 3,048,192 A | 8/1962 | Murphy, Jr. | |
| 3,276,472 A | 10/1966 | Jinkens, et al. | |
| 3,834,372 A | 9/1974 | Turney | |
| 3,957,082 A | 5/1976 | Fuson et al. | |
| 4,219,021 A | 8/1980 | Fink | |
| 4,566,480 A | 1/1986 | Parham | |
| 4,593,717 A | 6/1986 | Levasseur | |
| 4,608,996 A | 9/1986 | Brown | |
| 4,673,386 A | 6/1987 | Gordon | |
| 4,763,648 A | 8/1988 | Wyatt | |
| 4,796,644 A | 1/1989 | Polaschegg | |
| 4,830,013 A | 5/1989 | Maxwell | |
| 4,838,855 A | 6/1989 | Lynn | |
| 4,865,583 A | 9/1989 | Tu | |
| 4,900,322 A | 2/1990 | Adams | |

(Continued)

FOREIGN PATENT DOCUMENTS

WO    WO-89313341    12/1989

*Primary Examiner*—Max Hindenburg
*Assistant Examiner*—Adam J Eiseman
(74) *Attorney, Agent, or Firm*—Michael L. Crapenhoft

(57) ABSTRACT

A closed blood sampling system within a pressure monitoring line having a control valve that enables a clearance reservoir to be isolated from the pressure column when no samples are being taken. The valve is a stopcock-like device that includes a rotating valve member and attached control handle with clear visible and tactile indicators for the mode of operation. The rotating valve member has a number of internal and circumferential channels for connecting or disconnecting select ports in the core of the valve. By isolating the clearance reservoir, the quality of the pressure signal is improved such that the sampling line can be lengthened for greater convenience in the intensive care or operating room. The valve may also incorporate a blunt cannula sampling site therewithin.

27 Claims, 14 Drawing Sheets

U.S. PATENT DOCUMENTS

| | | | |
|---|---|---|---|
| 4,920,970 A | 5/1990 | Wyatt | |
| 4,928,694 A | 5/1990 | Maxwell | |
| 4,934,369 A | 6/1990 | Maxwell | |
| 4,951,669 A | 8/1990 | Maxwell et al. | |
| 4,967,797 A | 11/1990 | Manska | |
| 4,981,140 A | 1/1991 | Wyatt | |
| 5,002,066 A | 3/1991 | Simpson et al. | |
| 5,046,528 A | 9/1991 | Manska | |
| 5,048,525 A | 9/1991 | Maxwell | |
| 5,048,537 A | 9/1991 | Messinger | |
| 5,084,034 A | 1/1992 | Zanotti | |
| 5,089,421 A | 2/1992 | Dieffenbach | |
| 5,135,026 A | 8/1992 | Manska | |
| 5,148,811 A | 9/1992 | Messinger | |
| 5,178,607 A | 1/1993 | Lynn et al. | |
| 5,203,775 A | 4/1993 | Frank et al. | |
| 5,221,271 A | 6/1993 | Nicholson et al. | |
| 5,234,403 A | 8/1993 | Yoda et al. | |
| 5,265,621 A | 11/1993 | Simpson et al. | |
| 5,288,290 A | 2/1994 | Brody | |
| 5,324,266 A | 6/1994 | Ambrisco et al. | |
| 5,417,673 A | 5/1995 | Gordon | |
| 5,439,452 A | 8/1995 | McCarty | |
| 5,443,453 A | 8/1995 | Walker et al. | |
| 5,466,219 A | 11/1995 | Lynn et al. | |
| 5,466,228 A | 11/1995 | Evans | |
| 5,531,672 A | 7/1996 | Lynn | |
| 5,540,668 A | 7/1996 | Wilson, Jr. et al. | |
| 5,549,569 A | 8/1996 | Lynn et al. | |
| 5,643,218 A | 7/1997 | Lynn et al. | |
| 5,772,608 A | 6/1998 | Dhas | |
| 5,832,959 A | 11/1998 | Szymczakowski et al. | |
| 5,916,201 A | 6/1999 | Wilson, Jr. et al. | |
| 5,947,911 A | 9/1999 | Wong et al. | |
| 5,961,472 A | 10/1999 | Swendson et al. | |
| 6,126,618 A | 10/2000 | Bischof | |
| 6,156,019 A | 12/2000 | Langevin | |
| 6,158,467 A | 12/2000 | Loo | |
| 6,224,561 B1 * | 5/2001 | Swendson et al. | 600/562 |
| 6,269,704 B1 | 8/2001 | Ziv et al. | |
| RE37,357 E | 9/2001 | Lynn | |
| 6,287,265 B1 | 9/2001 | Gleason | |
| 6,364,847 B1 | 4/2002 | Shulze et al. | |
| 6,364,861 B1 | 4/2002 | Feith et al. | |
| 6,387,086 B2 | 5/2002 | Mathias et al. | |
| 6,418,966 B2 | 7/2002 | Loo | |
| 6,457,488 B2 | 10/2002 | Loo | |
| 6,508,778 B1 | 1/2003 | Verkaart et al. | |
| 6,626,884 B1 | 9/2003 | Dillon et al. | |
| 6,692,479 B2 | 2/2004 | Kraus et al. | |
| 6,843,775 B2 | 1/2005 | Hyun | |
| 6,871,665 B2 | 3/2005 | Hannah et al. | |
| 6,953,450 B2 | 10/2005 | Baldwin et al. | |
| 7,033,339 B1 | 4/2006 | Lynn | |
| 7,044,941 B2 | 5/2006 | Mathias et al. | |
| 7,087,047 B2 | 8/2006 | Kraus et al. | |
| 2001/0025167 A1 | 9/2001 | Kraus et al. | |
| 2002/0019621 A1 | 2/2002 | Mathias et al. | |
| 2002/0045912 A1 | 4/2002 | Ignotz | |
| 2002/0084437 A1 | 7/2002 | Nitsche et al. | |
| 2002/0156431 A1 | 10/2002 | Feith et al. | |
| 2002/0183651 A1 | 12/2002 | Hyun | |
| 2003/0125673 A1 | 7/2003 | Houde et al. | |
| 2003/0144607 A1 | 7/2003 | Mathias et al. | |
| 2003/0176813 A1 | 9/2003 | Mathias et al. | |
| 2003/0208151 A1 | 11/2003 | Kraus et al. | |
| 2004/0015147 A1 | 1/2004 | Mathias et al. | |
| 2004/0019344 A1 | 1/2004 | Peterson et al. | |
| 2004/0082898 A1 | 4/2004 | Mathias et al. | |
| 2004/0082899 A1 | 4/2004 | Mathias et al. | |
| 2004/0210162 A1 | 10/2004 | Wyatt et al. | |
| 2005/0096627 A1 | 5/2005 | Howard | |
| 2005/0143712 A1 | 6/2005 | Mathias et al. | |
| 2005/0148993 A1 | 7/2005 | Mathias et al. | |
| 2005/0187532 A1 | 8/2005 | Thurau | |
| 2006/0005886 A1 | 1/2006 | Parrino et al. | |
| 2006/0058773 A1 | 3/2006 | Raybuck | |
| 2006/0074350 A1 | 4/2006 | Cash | |
| 2006/0155212 A1 | 7/2006 | Madonia | |

* cited by examiner

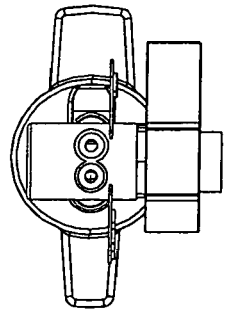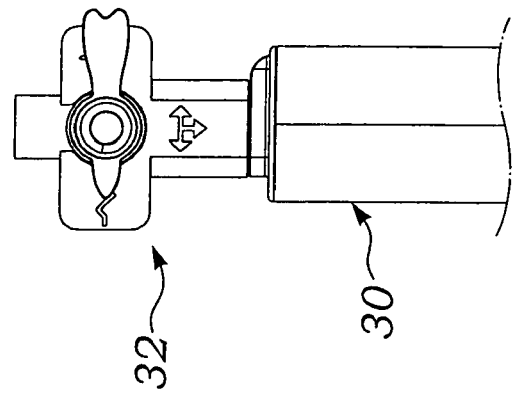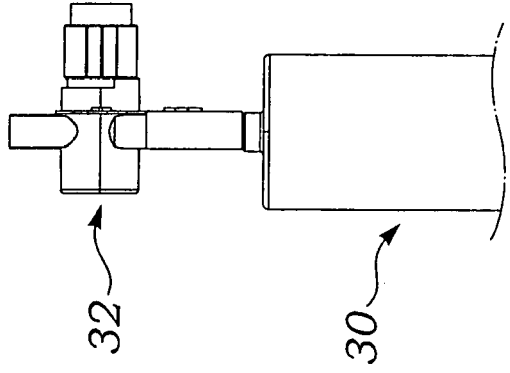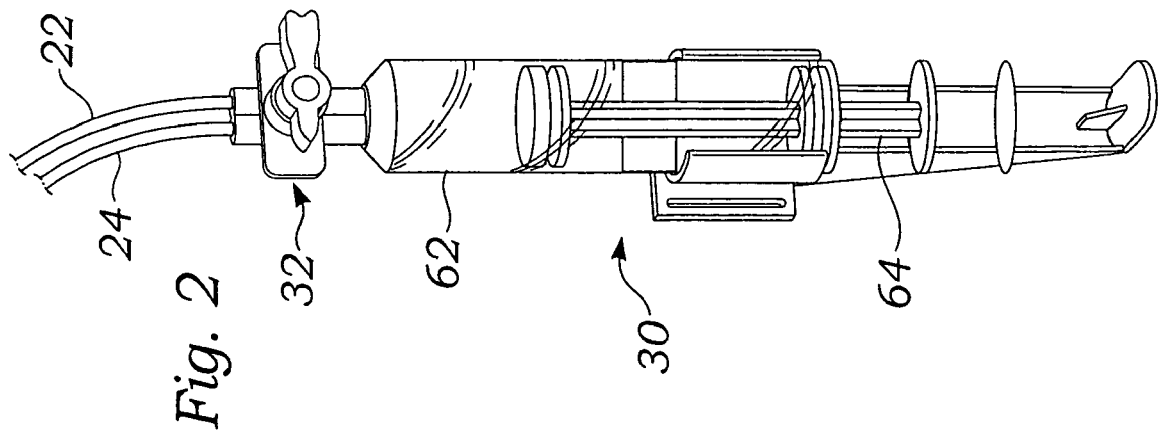

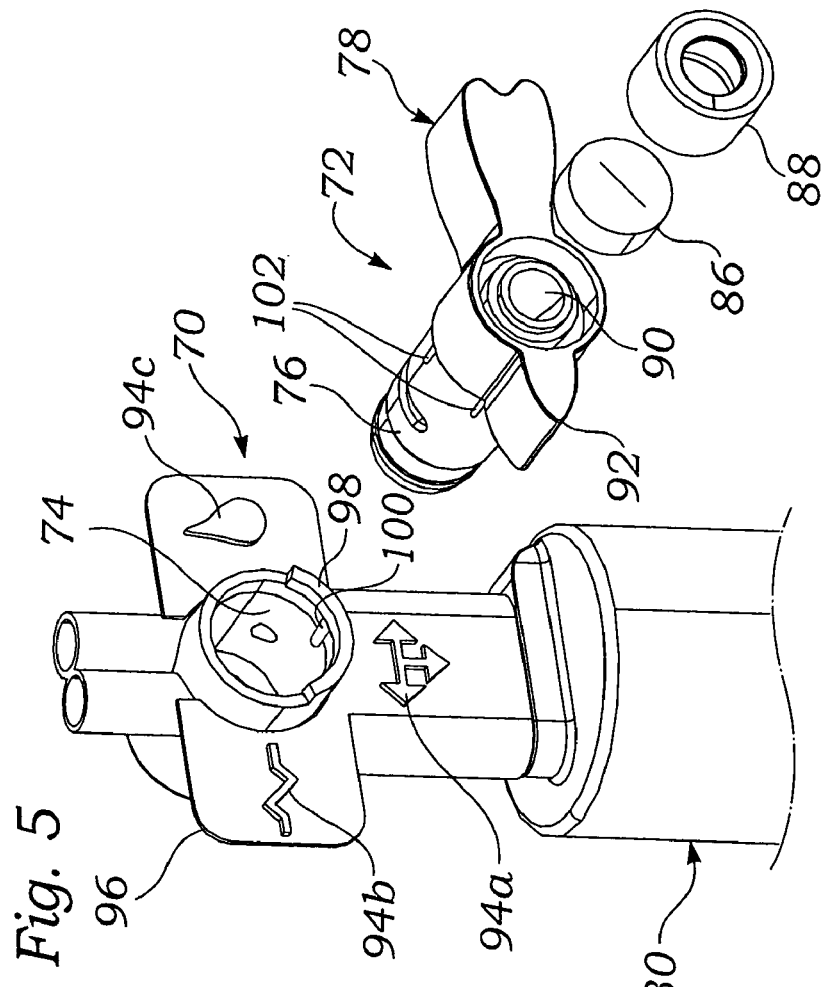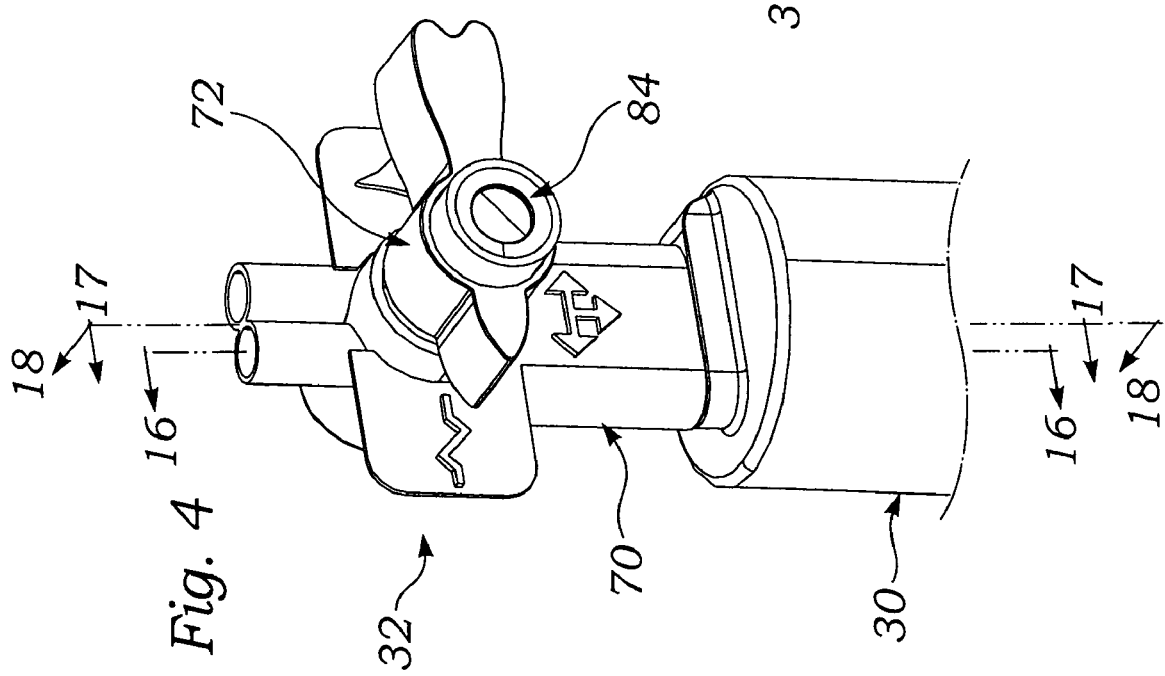

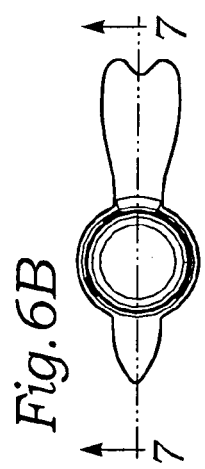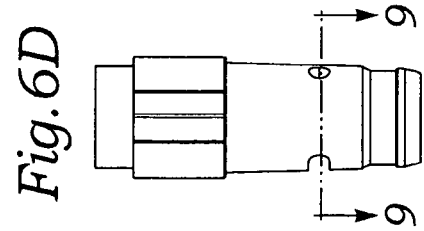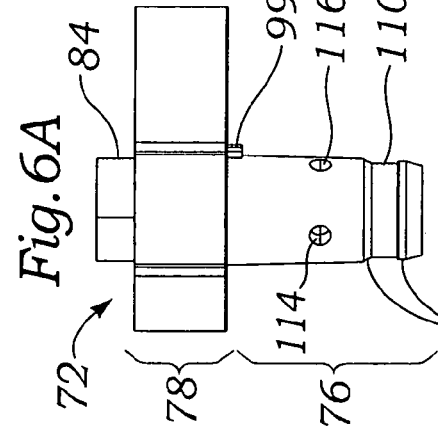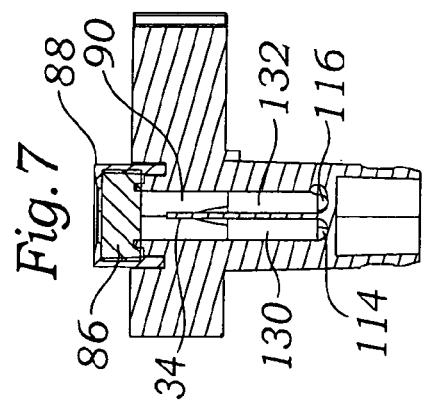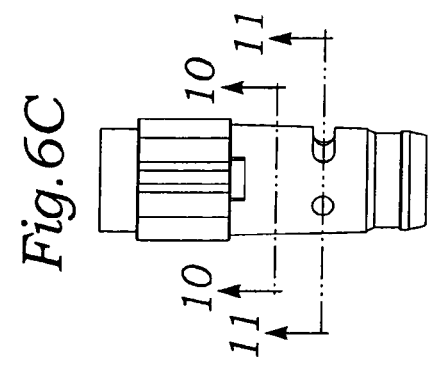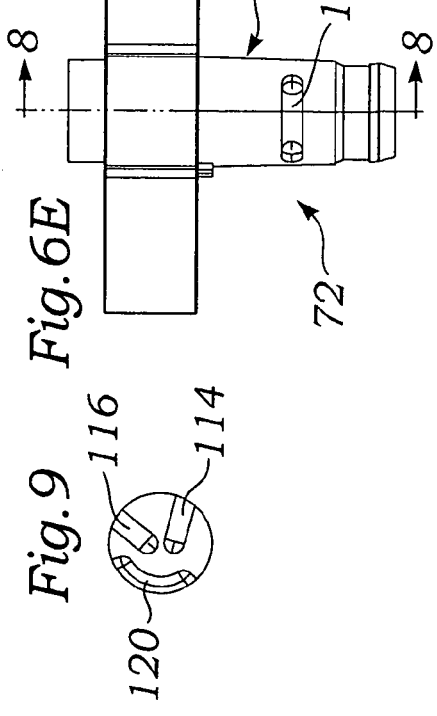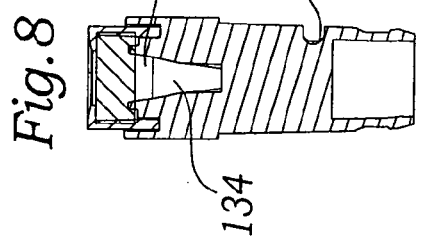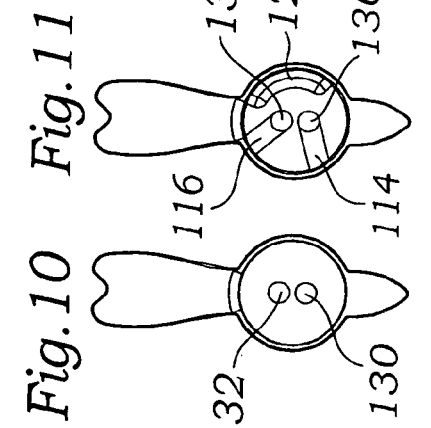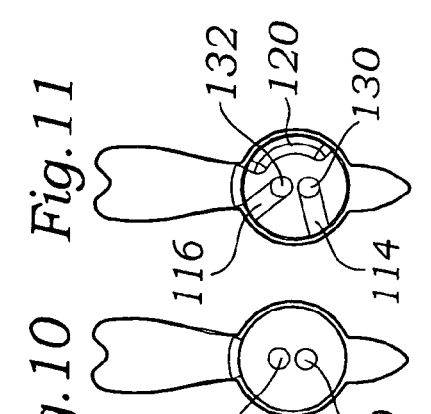

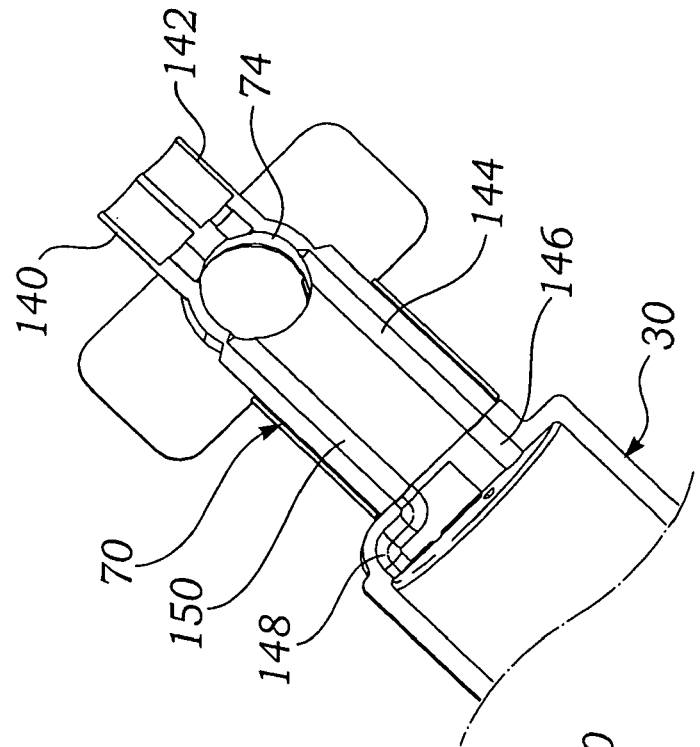
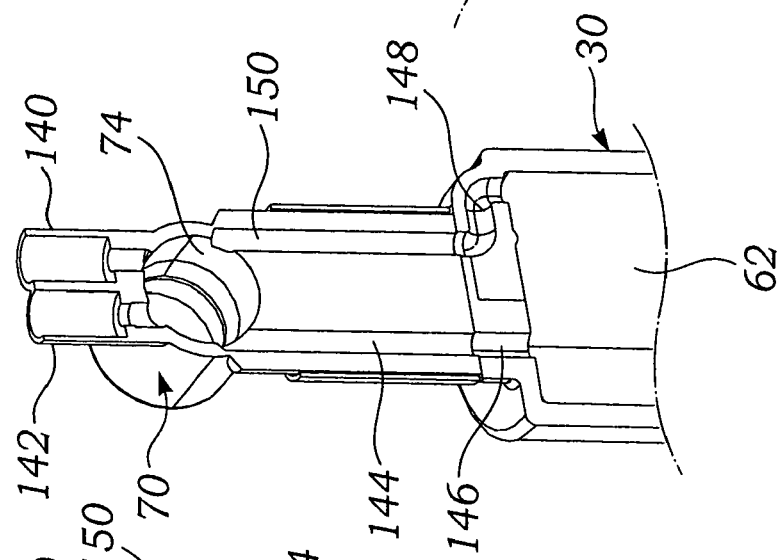
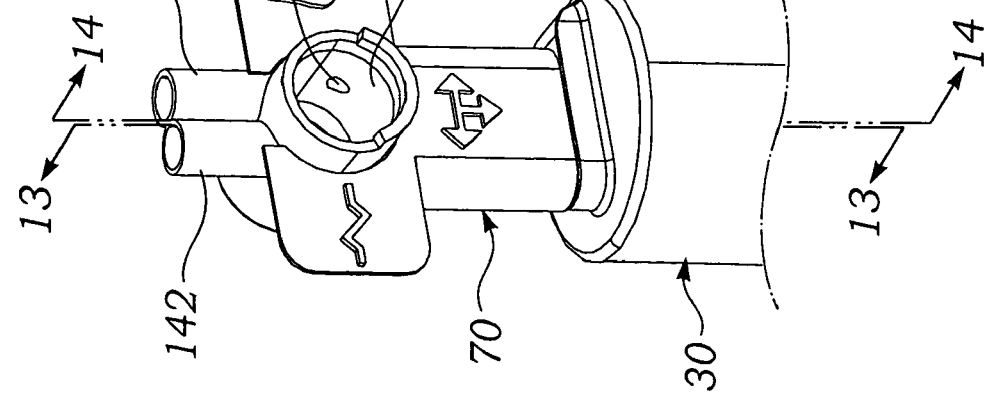

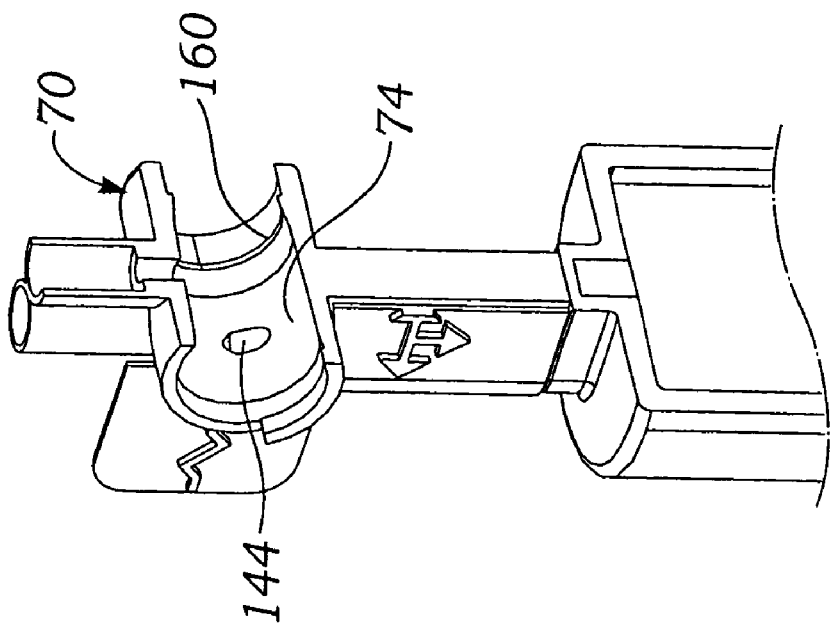
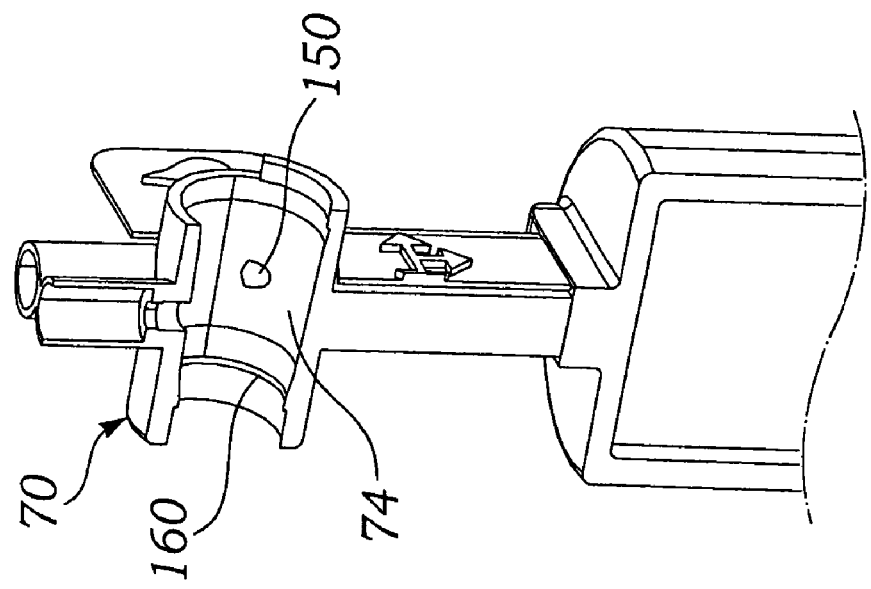

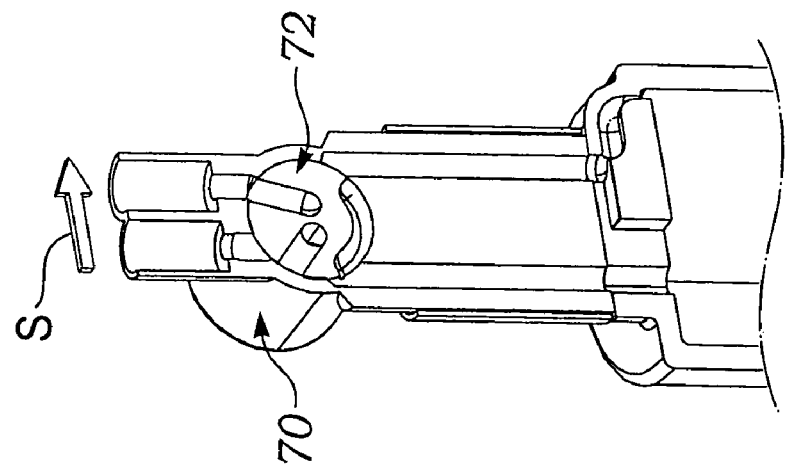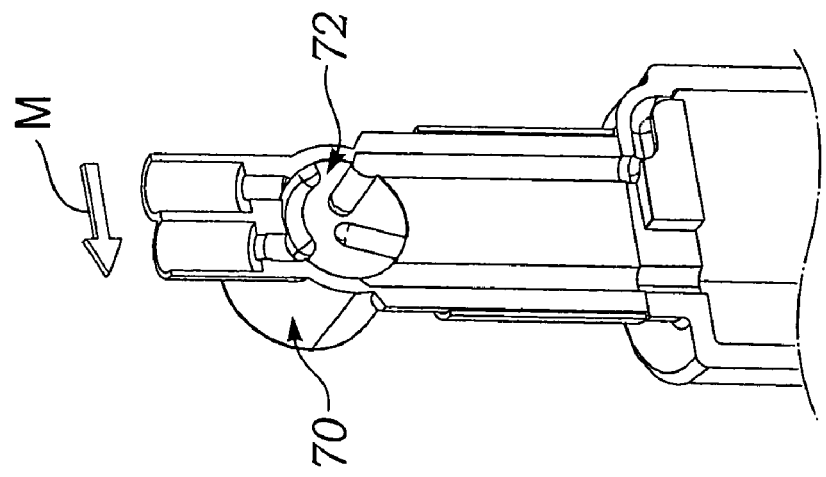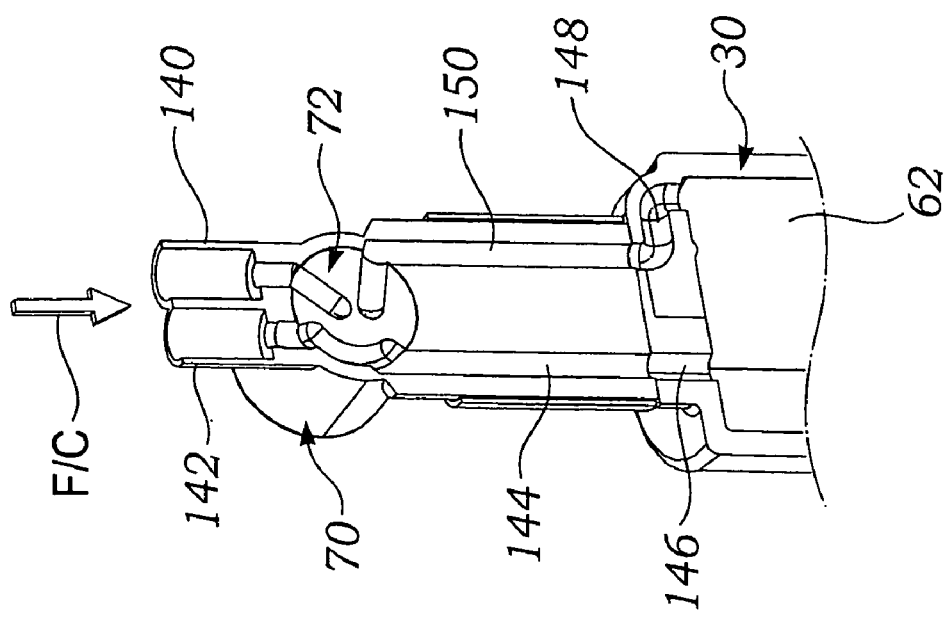

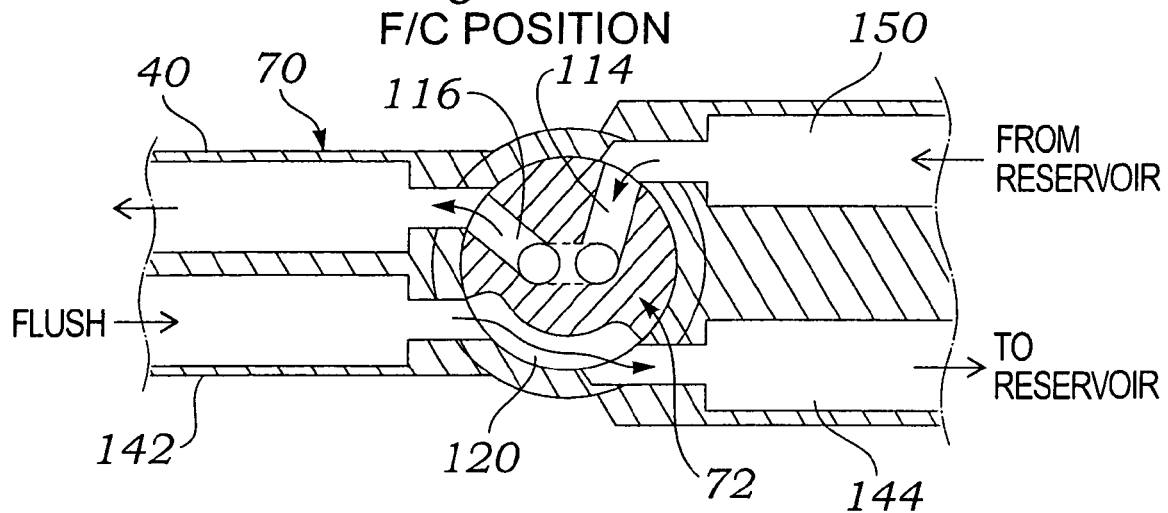
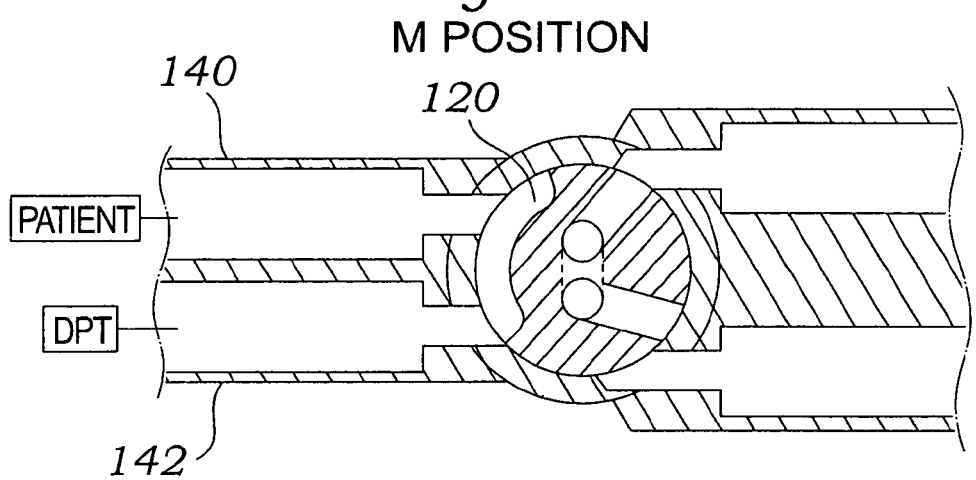
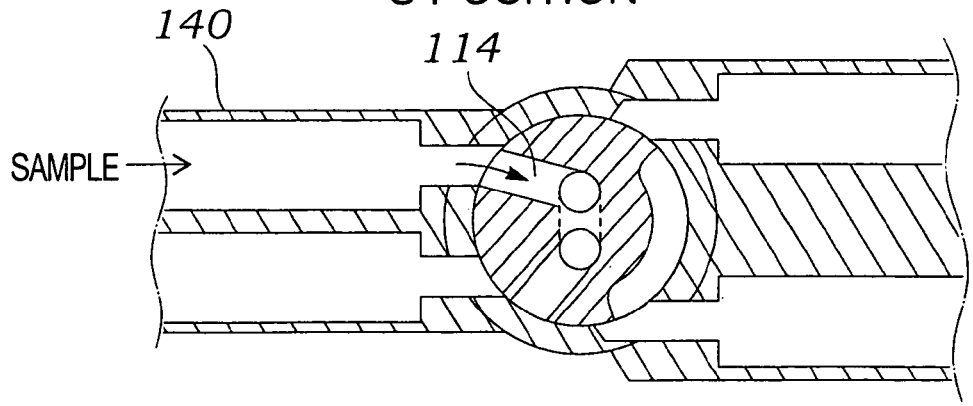

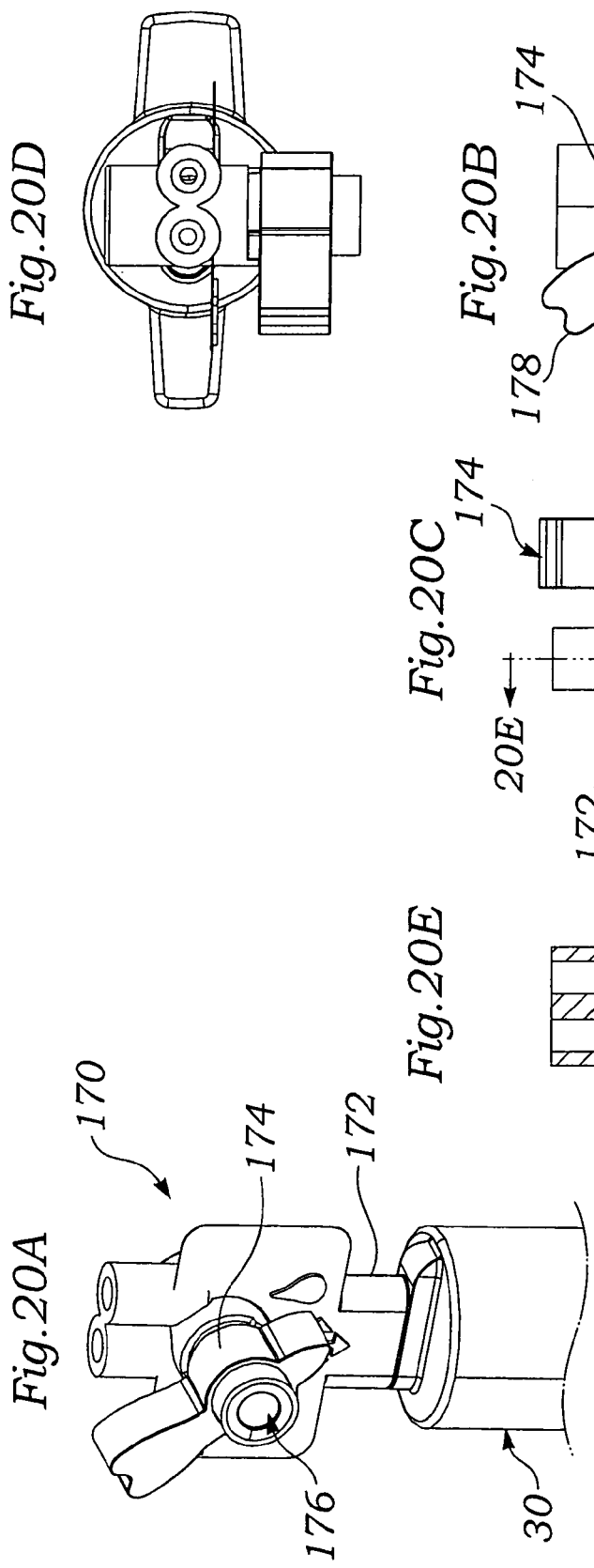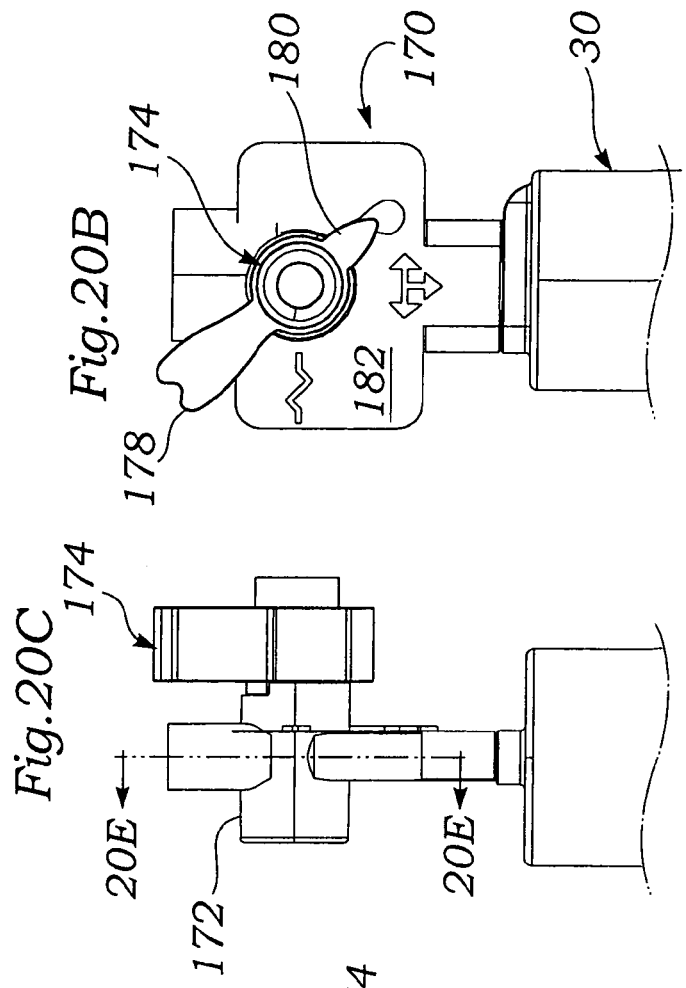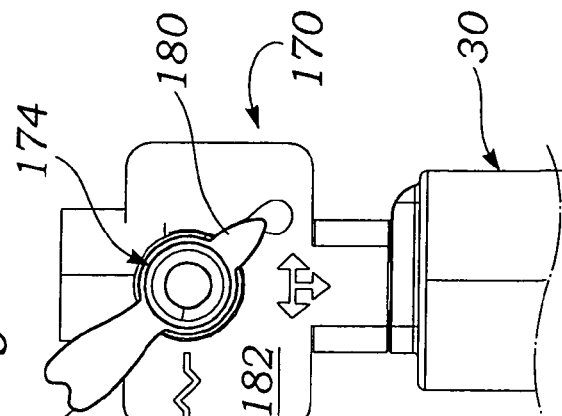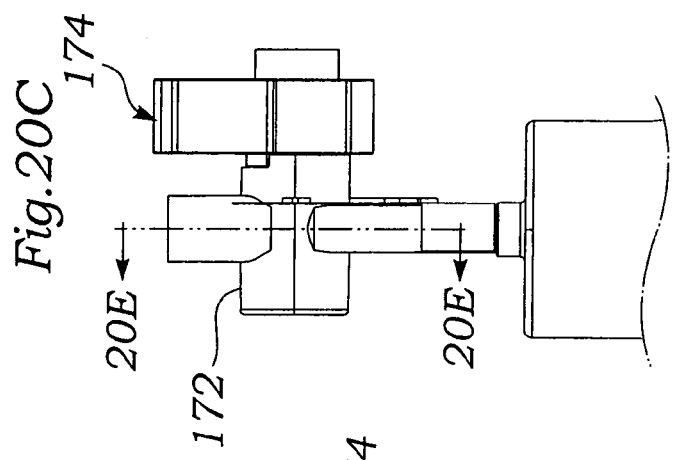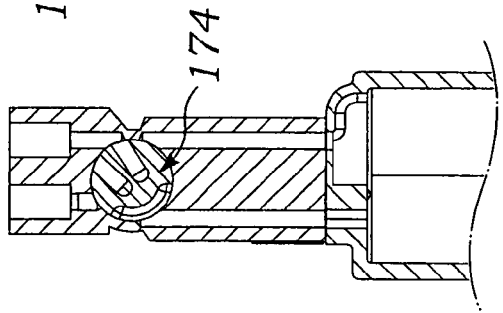

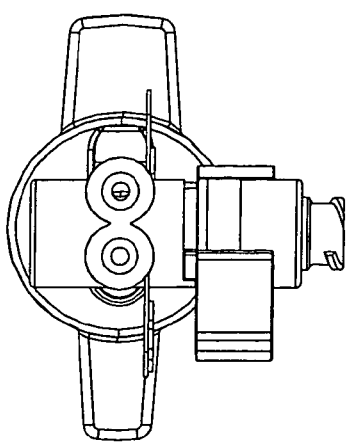
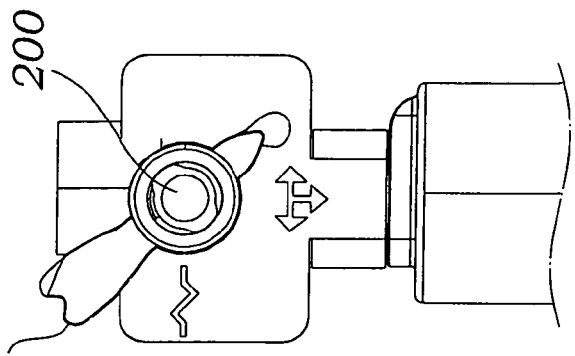
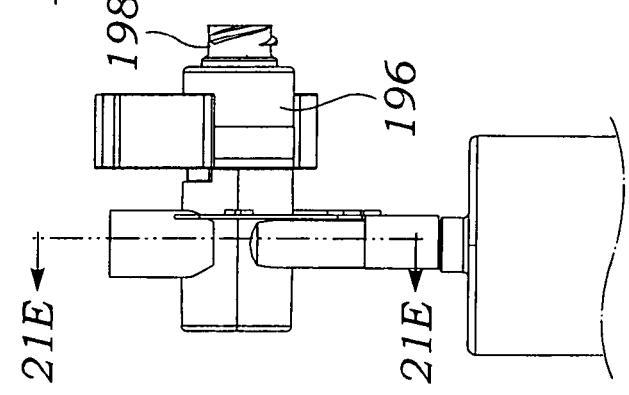
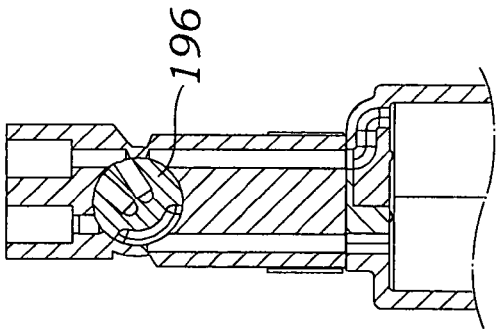
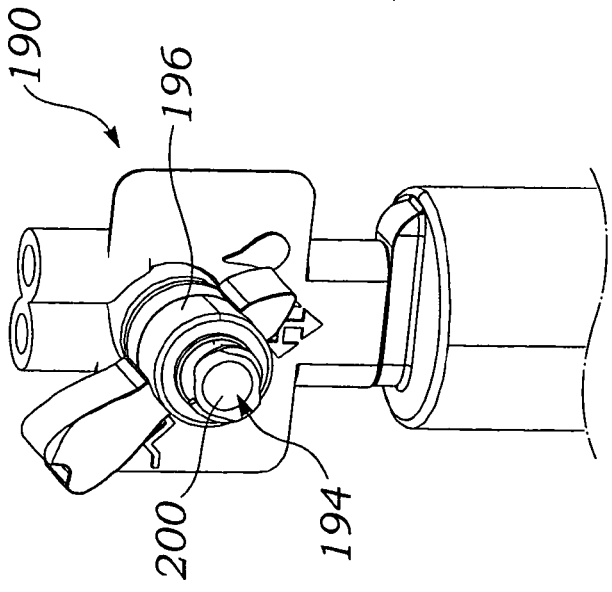

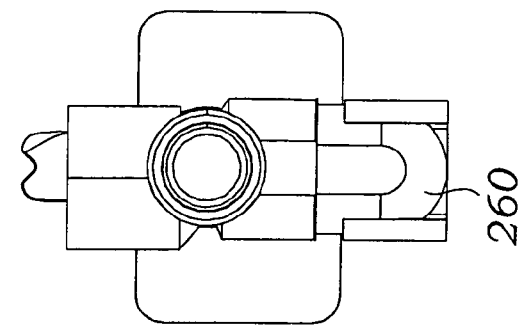
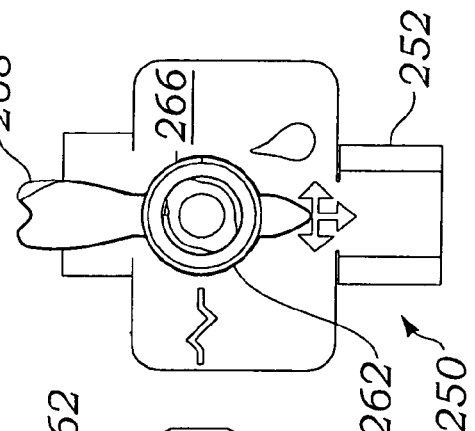
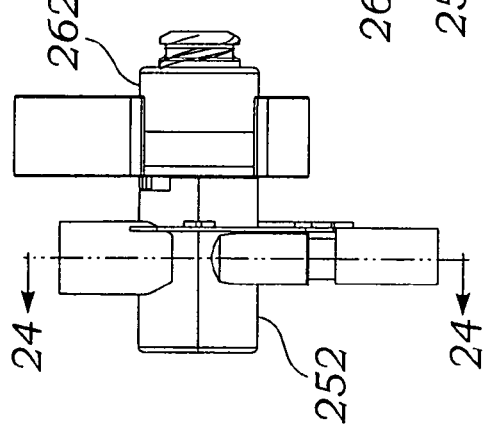
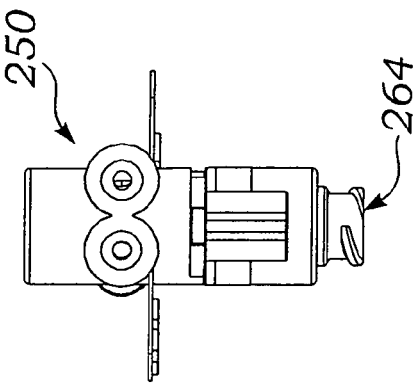
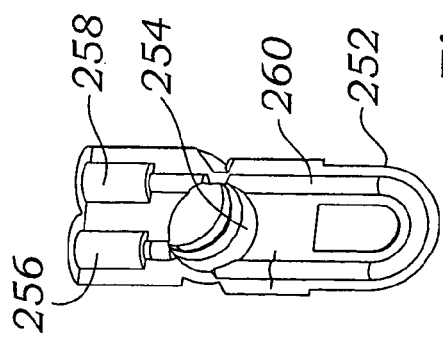
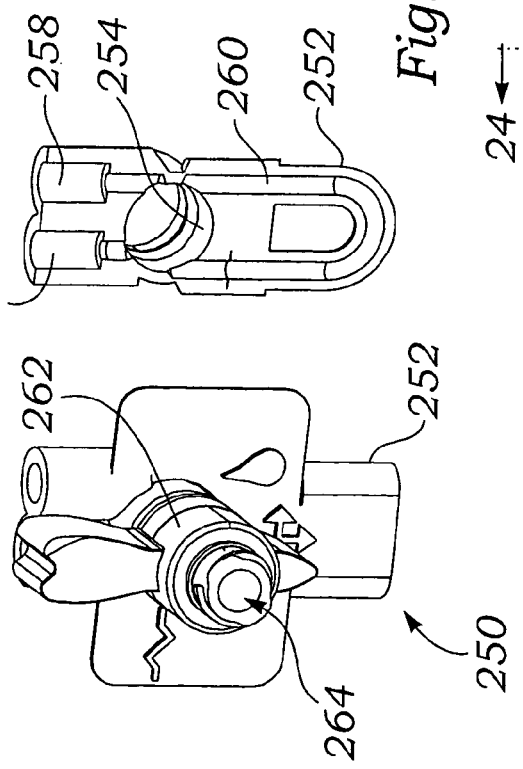

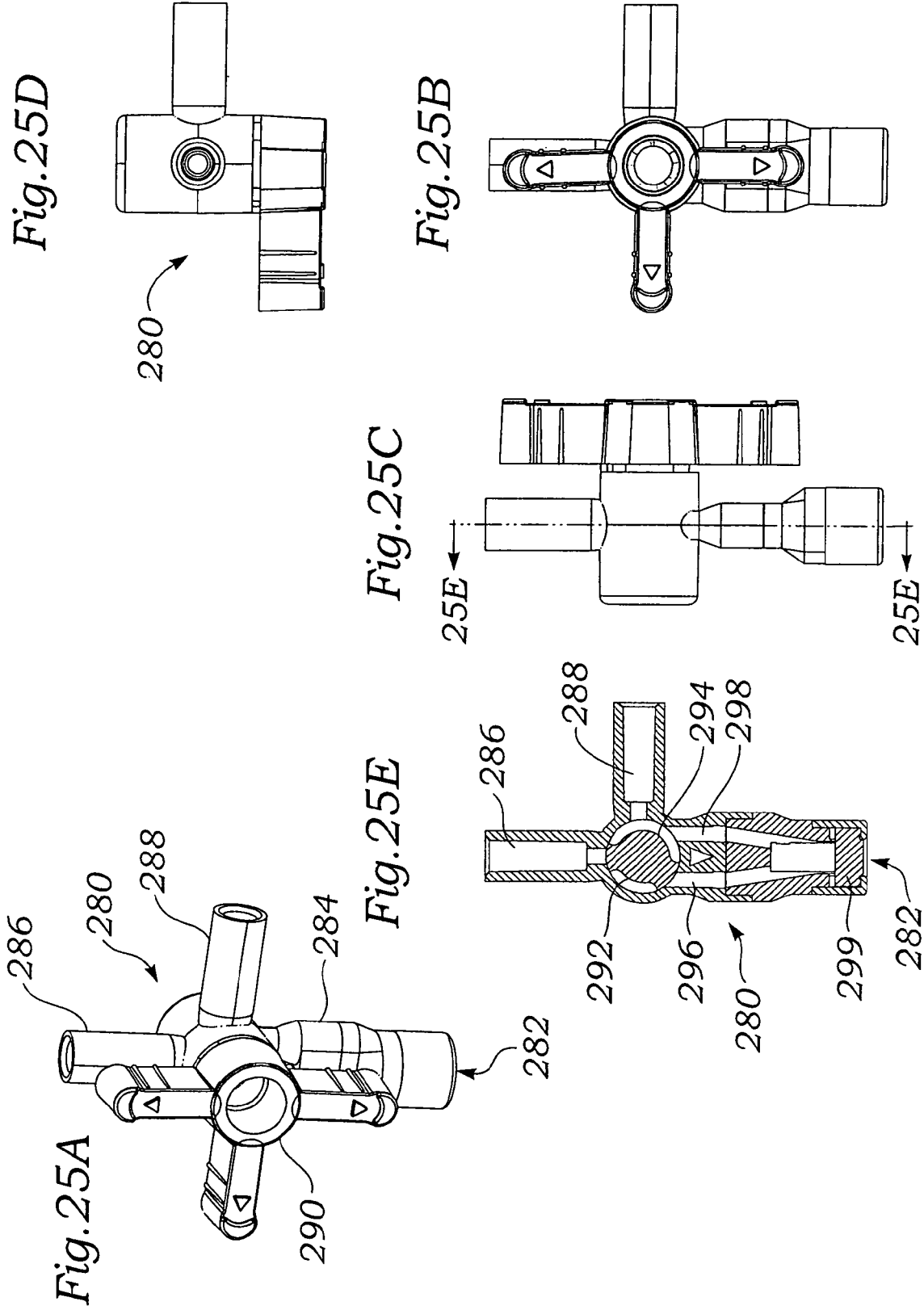

ced Sep. 13, 2005, and from provisional application No. 60/720,263, filed Sep. 21, 2005.

CLOSED BLOOD SAMPLING SYSTEM WITH ISOLATED PRESSURE MONITORING

RELATED APPLICATIONS

The present application claims the benefit of priority under 35 U.S.C. §119(e) from provisional application No. 60/717,119, filed Sep. 13, 2005, and from provisional application No. 60/720,263, filed Sep. 21, 2005.

FIELD OF THE INVENTION

The present invention relates to blood sampling systems and, in particular, to closed blood sampling systems with a clearing reservoir and pressure monitoring.

BACKGROUND OF THE INVENTION

In a hospital setting there is always the need to monitor patient health through the evaluation of blood chemistry profile. The simplest method employed in the hospital is to use a syringe carrying a sharpened cannula at one end and insert that cannula into a vein or artery to extract a blood sample from the patient. Patients that are in the critical care units or the operating room sometimes require as many as twelve samples a day. Such frequent sampling injections potentially expose the patient to airborne bacteria and viruses which can enter the bloodstream through the opening made by the sharpened cannula.

One way to obtain a blood sample is to draw the blood from a catheter that is already inserted in the patient, either in a central venous line, such as one placed in the right atrium, or in an arterial line. Typically, existing injection sites for arterial or venous drug infusion or pressure monitoring lines are used to take periodic blood samples from the patient. Conventional mechanisms for drawing blood from the lines used for infusion or pressure monitoring utilize a plurality of stopcock mechanisms that preclude flow from the infusion fluid supply or from the pressure column drip supply, while allowing blood to flow from the patient into a collecting syringe connected to a proximal port formed in one of the stopcocks. Typically, a blunt cannula through a slit septum is used to remove the danger of sticking the nurse or clinician, in a so-called "needle-less" system.

Most early systems required a two-step operation where a first sample of fluid, generally about 5 ml in volume for intensive care environments was withdrawn into the sampling syringe and discarded. This first sample potentially included some of the infusion fluid and thus would be an unreliable blood chemistry measurement sample. After the initial sample had been discharged, the second sample was pure blood from the artery or vein and was typically re-infused to the patient.

In response to the drawbacks associated with earlier two-step sampling systems, closed systems were developed as described in U.S. Pat. No. 4,673,386 to Gordon, and more recently in U.S. Pat. No. 5,961,472 to Swendson, which are expressly incorporated by reference herein. Commercial closed systems such as the Edwards VAMP® and VAMP Plus® Venous Arterial blood Management Protection systems of Edwards Lifesciences in Irvine, Calif. feature a reservoir in the tubing line from the patient that can draw fluid past a sampling port. The clearing volume is held in the in-line reservoir, and not set-aside in a syringe for re-infusion later. The sampling systems are often used in conjunction with a pressure monitor having a transducer continually or periodically sensing pressure within the sampling line except during the draw of a blood sample.

The VAMP Plus® system conveniently utilizes a reservoir with one-handed operability, and includes a line from the patient into and out of the reservoir and to a proximal source of flushing fluid and a pressure transducer. (The standard directional nomenclature is that proximal is toward the clinician, or away from the patient, and distal is toward the patient). A stopcock valve at the reservoir controls the mode of operation. Prior to drawing a blood sample, the reservoir plunger is latched closed, though a reservoir gap allows a continuous drip of IV flushing fluid through an inlet port to an outlet port. A pressure transducer in the line proximal to the reservoir senses fluid pressure within the line and conveys the signal to a monitor. One exemplary pressure transducer used with both the VAMP® and VAMP Plus® systems is the Edwards TruWave® Disposable Pressure Transducer.

When a blood sample is to be taken, the flow of flushing or infusion fluid is halted by turning the handle of the reservoir stopcock valve. The nurse or clinician then withdraws an amount of fluid into the reservoir chamber and distal line sufficient to pull pure blood past one or more fluid sampling sites. After full retraction of the plunger, the stopcock valve closes off the reservoir from the patient and a sample of blood is taken at one or the other sampling sites. Subsequently, the clinician manipulates the stopcock valve so that the volume within the reservoir can be reinfused back into the patient by depressing the plunger, and the flushing drip and pressure monitoring resumes.

In the closed blood sampling/pressure monitoring systems described above, the pressure transducer typically includes a diaphragm exposed to the in-line fluid on one side and has a device for measuring deflection of the diaphragm on the other. Such pressure lines typically make use of relatively stiff tubing primed with a suitable physiological fluid such as saline or 5% dextrose solution as a pressure column. For adults, a bag pressurized with air surrounds the fluid supply bag to maintain a constant pressure differential in the line urging fluid toward the patient through a restrictor orifice. The slow drip of physiological fluid flushes the line to prevent clotting. Some transducers such as the TruWave® Disposable Pressure Transducer include a flush device that also can be used for sending transient pressure waves through the line. A Snap-Tab™ device of the TruWave® is a rubber tab which when pulled and then released sends a square wave through the pressure column to check the inherent frequency response of the entire system, which includes the tubing and any components attached thereto, such as the sampling ports and reservoir. Proper system frequency response is necessary for reliable blood pressure measurements. In general, a more accurate signal may be obtained with a shorter sampling line and fewer components so that the transducer is closer to the patient and there is less delay between the generation and receipt of the blood pressure signal, and less interference. However the limited amount of space available or the location of the anesthesiologist during a surgical procedure often necessitates a relatively long tubing line which degrades the signal. Furthermore, minimum functionality of the system requires various components such as sampling sites be included.

In view of the foregoing, there is a need for a blood sampling system used in conjunction with a pressure transducer that produces more accurate pressure readings.

SUMMARY OF THE INVENTION

The present invention provides a fluid sampling system within a pressure monitoring line having a control valve that enables a clearance reservoir to be isolated from the pressure column when no samples are being taken. The control valve further permits complete flushing of the system with no dead spaces. Additionally, control valve desirably incorporates a sampling port therein capable of isolating the sampling port from the clearance reservoir. By isolating the clearance reservoir, the quality of the pressure signal is improved such that the sampling line can be lengthened for greater convenience in the intensive care or operating room.

In accordance with a first embodiment of the invention, a medical system for fluid sampling and pressure monitoring of a fluid system of a patient is provided. The system includes a conduit line with a proximal segment adapted to be supplied with a physiological fluid (e.g., saline) and a distal segment adapted to be in communication with a fluid system of a patient. A control valve has a manifold defining an interior chamber. The manifold has a proximal port fluidly connected to the proximal segment, a distal port fluidly connected to the distal segment, and a reservoir port, wherein each of the manifold ports opens to the interior chamber. A system further includes a fluid sampling port and pressure transducer connected to the conduit line for sensing the pressure of the fluid therein. A reservoir fluidly communicates with the reservoir port of the control valve manifold. The control valve further includes a valve member movable within the interior chamber and having channels therein that selectively communicate with the manifold ports. The valve member is movable into at least two positions:

a first position that provides open fluid communication from the proximal segment to the patient through the control valve so as to eliminate any dead spaces therein, wherein reduced pressure within the reservoir pulls fluid from the distal segment through the control valve and into the reservoir sufficient to draw fluid from the fluid system of the patient past the sampling port, and a second position that provides open fluid communication from the proximal segment to the proximal port and through at least one channel in the valve member to the distal segment while bypassing the reservoir, such that the pressure of fluid within the conduit line exclusive of the reservoir can be sensed by the pressure transducer.

Desirably, the valve member also has a third position that provides open fluid communication from the distal segment to the sampling port but prevents communication between the sampling port and both the reservoir and the proximal segment.

In a preferred embodiment the valve member comprises a core rotatable within the interior chamber of the manifold and a control handle external to the manifold, wherein mating features on the valve member core and manifold provide tactile feedback and positive positioning of the core in both first and second positions. Alternatively, or in addition, coordinated visible features on the control handle and manifold provide symbolic indicators of both first and second positions of the valve member.

The sampling port may be formed within the control valve or along the distal segment of the conduit line. If within the control valve, the sampling port may be formed within the valve member and communicates with a sampling cavity formed internally within the valve member open to at least one of the channels. Alternatively, the sampling port connects to the control valve manifold and defines a flow path therethrough whose opposite ends open to the interior chamber of the manifold. Furthermore, the system may include a second sampling port having a sampling cavity positioned along the distal segment of the conduit line.

In accordance with one embodiment, the valve member comprises a core movable within the interior chamber of the manifold and a control handle external to the manifold, the core having an external channel formed along an exterior surface of the core and an internal channel formed along an interior bore of the core. The internal channel desirably opens to the exterior surface of the core at two separated locations spaced from the external channel.

System further may include means for pressurizing the physiological fluid such that at least some fluid continues to flow through the conduit line to the patient when the valve member is in the first position. Desirably, the reservoir has an inlet open to an outlet port of the control valve manifold and an outlet open to an inlet port of the control valve manifold. In this embodiment, the first position of the valve member provides open fluid communication between the control valve flow passages through the inlet and outlet of the reservoir to flush a chamber of the reservoir.

A second embodiment of the present invention comprises a medical system for fluid sampling of a fluid system of a patient. The system encompasses a conduit line with a proximal segment adapted to be supplied with a physiological fluid and a distal segment adapted to be in communication with a fluid system of a patient. A control valve connects between the proximal segment and the distal segment of the conduit line. A fluid sampling port defines a flow path therethrough whose opposite ends open to internal channels in the control valve. A reservoir fluidly communicates with a reservoir port of the control valve manifold. The control valve further includes a valve member movable into at least three positions:

a first position that provides open fluid communication from the proximal segment through the control valve to the distal segment, a second position that provides open fluid communication from the proximal segment to the distal segment while bypassing the reservoir and sampling port, and a third position that provides open fluid communication from the distal segment to the sampling port but prevents communication between the sampling port and both the reservoir and the proximal segment.

Desirably, the control valve further includes a manifold defining an interior chamber. The manifold has a proximal port fluidly connected to the proximal segment of the conduit line, a distal port fluidly connected to the distal segment, an outlet port, and an inlet port, wherein each of the manifold ports opens to the interior chamber. The valve member also comprises a core movable within the interior chamber of the manifold and having channels therein that selectively communicate with the manifold ports. The reservoir has an inlet open to the manifold outlet port and an outlet open to the manifold inlet port. In this embodiment:

the first position provides open fluid communication from the proximal segment to the proximal port and the outlet port of the control valve, through the inlet and outlet of the reservoir, to the inlet port and the distal port of the control valve to the distal segment, the second position provides open fluid communication from the proximal segment to the proximal port and through at least one channel in the valve member core to the distal segment while bypassing the reservoir and sampling port, and the third position provides open fluid communication from the distal segment to distal port and one of the channels of the valve member core, and to the sampling port.

The valve member core may have an external channel formed along an exterior surface of the core and an internal channel formed along an interior bore of the core. Desirably, the internal channel opens to the exterior surface of the core at two separated locations spaced from the external channel.

Another aspect of the invention is a method of taking samples and measuring the pressure of a fluid system of a patient. The method provides a fluid sampling system with a conduit line and a reservoir connected thereto between a proximal segment adapted to be supplied with a physiological fluid and a distal segment adapted to be in communication with a fluid system of a patient. A control valve interposed between the reservoir and the conduit line has a movable valve member with a control handle, the valve member movable into at least a first position and a second position. A pressure transducer connects to the conduit line for sensing the pressure of the fluid therein, and a fluid sampling port is provided in the sampling system.

The method includes selecting the first position of the valve member to provide open fluid communication from the proximal segment to the distal segment via the control valve and the reservoir, and creating a reduced pressure within the reservoir such that fluid flows from the distal segment through the control valve into the reservoir sufficient to draw fluid from the fluid system of the patient past the sampling port. The method further includes selecting the second position of the valve member to provide open fluid communication from the proximal segment to the distal segment via the control valve while bypassing the reservoir, and monitoring the pressure sensed by the pressure transducer. Desirably, the valve member has a third position, and the method includes selecting the third position of the valve member to provide open fluid communication from the distal segment to the sampling port but prevent communication between the sampling port and both the reservoir and the proximal segment, and sampling fluid from the conduit line through the sampling port.

In a preferred embodiment, the fluid system of the patient is the blood system, and the method further including means for pressurizing the physiological fluid such that at least some fluid continues to flow through the conduit line to the patient when the valve member is in the first position. In this instance, the method including the steps of:

selecting the first position of the valve member such that the physiological fluid flows through the conduit line to the patient; then creating a reduced pressure within reservoir and collecting sufficient fluid therein such that blood flows past the sampling port; then selecting the third position of the valve member; then sampling blood from the conduit line through the sampling port; then creating an elevated pressure within the reservoir to expel blood therefrom into the distal segment of the conduit line; then selecting the first position of the valve member such that the physiological fluid flows through the conduit line to the patient and flushes the reservoir of blood; and then selecting the second position of the valve member and monitoring the pressure sensed by the pressure transducer.

Preferably, the control valve has a manifold defining an interior chamber within which the valve member rotates, and further including mating features on the valve member and manifold that provide tactile feedback and positive positioning of the core in both first and second positions, the method of selecting the first and second positions further including rotating the valve member until the tactile feedback is sensed. Or, the control valve includes visible features that provide symbolic indicators of the first and second positions of the control handle, the method of selecting the first and second positions further includes interpreting the symbolic indicators to determine the placement of the control handle corresponding to the first and second positions.

Another useful aspect of the present invention is a medical system for fluid sampling of a fluid system of a patient. The sampling system includes a conduit line with a proximal end adapted to be supplied with a physiological fluid and a distal end adapted to be in communication with a fluid system of a patient. A pressure transducer connects to the conduit line for sensing the pressure of the fluid therein, and a fluid sampling port is provided having a sampling cavity. A control valve interposes between the conduit line and the sampling port and has a manifold defining an interior chamber. The manifold further includes a proximal port fluidly connected to the conduit line, a distal port fluidly connected to the conduit line, an outlet port, and an inlet port, wherein each of the manifold ports opens to the interior chamber. The control valve also has a valve member movable within the interior chamber and having channels therein that selectively communicate with the manifold ports, the valve member being movable into at least three positions:

a first position that provides open fluid communication from the conduit line to the proximal port and the outlet port of the control valve to the sampling cavity, and to the inlet port and the distal port of the control valve to the conduit line, a second position that provides open fluid communication from the conduit line to the proximal port and through at least one channel in the valve member and back to the conduit line while bypassing the sampling port, such that the pressure of fluid within the conduit line exclusive of the sampling port can be sensed by the pressure transducer, and a third position that provides open fluid communication from the distal end of the conduit line through the control valve to the sampling port but prevents communication between the sampling port and the proximal end of the conduit line.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

FIG. 2 is a perspective view of a reservoir of the fluid sampling system in FIG. 1 having an attached control valve of the present invention;

FIGS. 3A-3C are several orthogonal views of one end of the reservoir showing the control valve;

FIG. 4 is a close-up perspective view of the control valve on the end of the reservoir having a central sampling port in a rotatable valve member;

FIG. 5 is an exploded perspective view of the control valve;

FIGS. 6-11 are various external and sectional views of the rotatable valve member used in the control valve shown in FIGS. 4 and 5;

FIGS. 12-15 are various external and sectional views of a manifold of the control valve of FIGS. 4 and 5;

FIGS. 18A-18C are axial sectional views of the control valve taken along line 18-18 of FIG. 4 showing the positions of interior fluid flow channels for different positions of the valve member;

FIGS. 19A-19C are views similar to FIGS. 18A-18C of the interior fluid flow channels for the three different positions of the control valve showing selective interconnections between the various manifold ports;

FIGS. 20A-20E are various external and sectional views of an alternative control valve of the present invention with a different arrangement of internal flow paths and a central sampling port;

FIGS. 21A-21E are various external and sectional views of an alternative control valve with a different arrangement of internal flow paths and a luer-style central sampling port;

FIGS. 23A-23E are various external views of a luer-style valved sampling port;

FIG. 24 is an axial sectional view of the valved sampling port of FIGS. 23A-23E; and FIGS. 25A-25E are various external and sectional views of a further alternative valved sampling port with the sampling port extending from the side of a manifold.

DETAILED DESCRIPTION OF THE PREFERRED EMBODIMENTS

The present invention provides an improved closed blood sampling system in conjunction with pressure monitor. As mentioned above, continuous or periodic blood pressure monitoring is a common and extremely useful tool in the intensive care or operating room. However, it should be mentioned that the apparatuses and methods described herein could be utilized in conjunction with any fluid system of a patient which would benefit from pressure monitoring. For instance, intracranial pressures could be monitored and cerebrospinal fluid samples taken by placing the system described herein in fluid communication with an intraventricular catheter. Therefore, the appended claims cover the sampling and monitoring of any fluid system within a patient unless otherwise specified.

The present invention comprises an improved, closed, one-handed fluid sampling system especially useful for sampling blood in the operating room or critical care unit (CCU). The overall functioning of the system is similar to those in the prior art, in particular the VAMP Plus® Venous Arterial blood Management Protection system available from Edwards Lifesciences of Irvine, Calif. Furthermore, the blood sampling function is desirably combined with a pressure transducer and monitoring hardware. The term "closed fluid sampling system" should be understood to include both systems that have a dedicated reservoir (i.e., one that remains connected) and that utilize a removable reservoir (or syringe) that gains access to the fluid column through a port. As explained above, dedicated reservoirs are preferred because of their enhanced sterility, but the feature of the present invention that isolates the reservoir from the fluid pressure column may also be useful with removable reservoirs.

Figure 1:
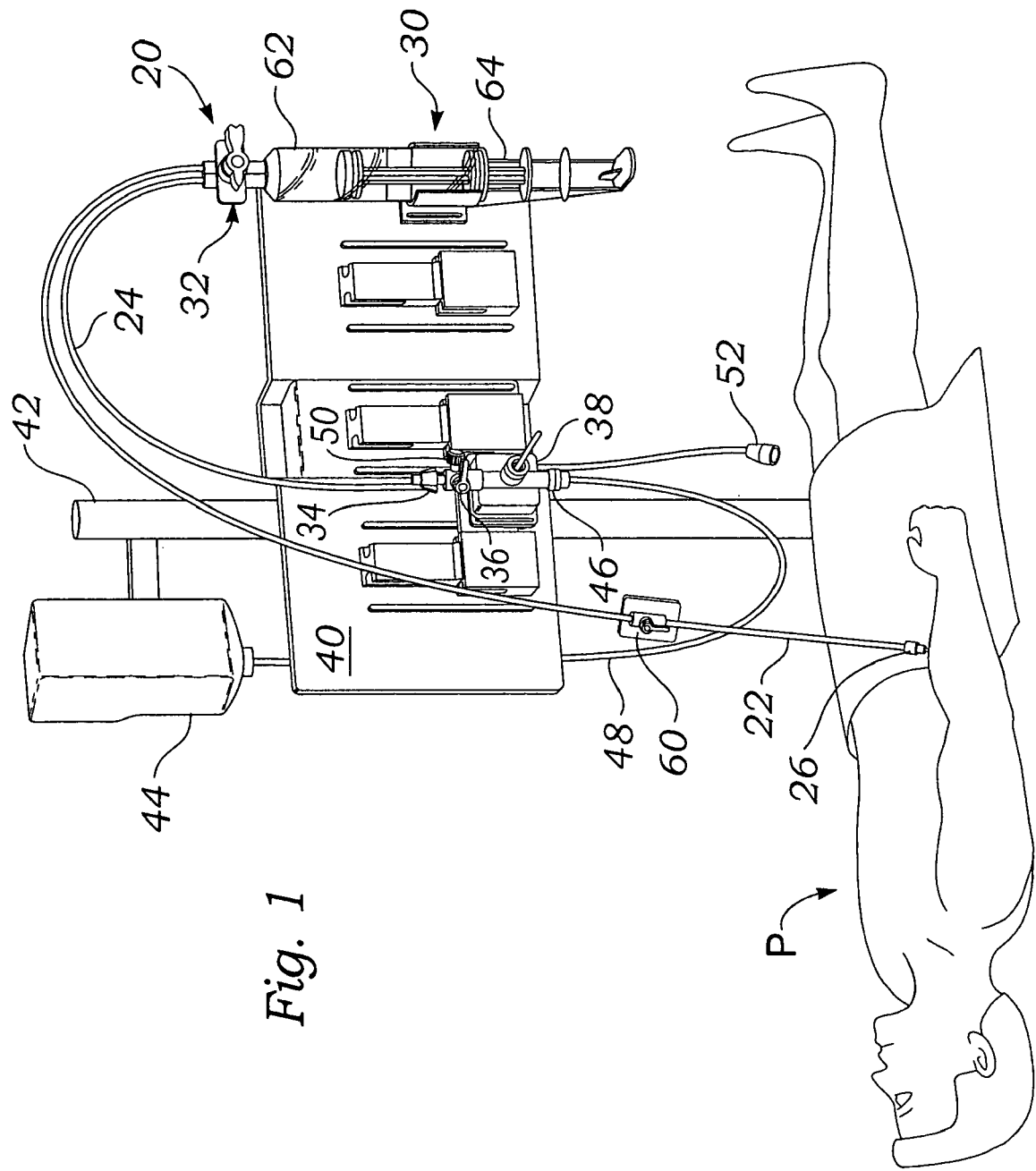
FIG. 1 illustrates a typical hospital room setup of a fluid sampling system of the present invention incorporating a reservoir, the sampling port, and a pressure transducer within a conduit line to a patient.

FIG. 1 illustrates an exemplary blood sampling system 20 of the present invention in the environment of a typical set up in a hospital room and connected to a patient P. The blood sampling system 20 comprises a conduit line having a distal segment 22 toward the patient and a proximal segment 24. The conduit line is primarily medical grade pressure tubing. The distal segment 22 may terminate in a male luer connector 26 for attaching to a female luer connector (not shown) of an injection site, or other conduit leading to the patient. A reservoir 30 connects to the conduit line via a control valve 32 interposed between the distal segment 22 proximal segment 24. The control valve 32 externally resembles a stopcock and controls fluid flow between the conduit line and the reservoir 30.

The proximal segment 24 extends from the control valve 32 and terminates in a female luer connector 34 attached to a stopcock 36 of a pressure transducer 38. The reservoir 30 and pressure transducer 38 removably mount to a bracket 40 which, in turn, may be secured to a conventional pole support 42 with the reservoir in a vertical orientation.

As mentioned above, the blood sampling system 20 forms a portion of a pressure monitoring system, and the fluid pressure transducer 36 may be a TruWave™ Disposable Pressure Transducer available from Edwards Lifesciences of Irvine, Calif. A supply of flush solution 44 connects to a flush port 46 of the transducer 38 via tubing 48. Typically for adults, the flush solution 44 comprises a bag of physiological fluid such as saline surrounded by a pressurized sleeve that squeezes the fluid and forces it through the tubing 48. In addition, an infusion fluid supply (not shown) may be provided in communication with an infusion port 50 of the stopcock 36. The pressure transducer 38 is thus placed in fluid communication with the arterial or venous system of the patient through the conduit line, and preferably includes a cable and plug 52 to connect to a suitable display monitor (not shown). Though the pressure transducer 38 is shown positioned within the proximal segment 24, it could also be located in the distal segment 22.

The sampling system 20 further comprises a fluid sampling site 60 that desirably defines a Z-shaped flow passage adjacent a pre-slit septum (not numbered). With this configuration, a minimal amount of flush volume is needed to clear the line after sampling. The septum preferably comprises an elastomeric disc which accepts a blunt cannula and reseals after each sample is drawn, reducing the potential for contamination and eliminating the danger of needle sticks. Such sampling site is described in U.S. Pat. No. 5,135,489 to Jepson, et al., which is hereby expressly incorporated by reference.

FIG. 2 better illustrates one embodiment of a blood sampling reservoir 30 of the present invention removed from the bracket 40. The reservoir 30 desirably includes a syringe-type variable volume chamber 62, though other reservoirs that have constant volume chambers or other receptacles for receiving fluid may be used. Preferably, the reservoir 30 is of a type that includes a constantly open flow channel through the variable volume chamber 62 for passage of flushing fluid therethrough. A particularly useful such reservoir 30 is the Edwards VAMP Plus® system mentioned above.

In one mode of operation of the system 20, a reduced pressure is created within the variable volume chamber 62 by withdrawing the plunger 64 such that a fluid sample from the distal segment 22 is drawn into the chamber. The chamber 62 has a sufficient volume, typically 12 ml, to draw blood from the patient P passed the sampling site 60. The clinician can then take a sample of undiluted blood from the site 60. Subsequently, the blood and other fluids drawn into the reservoir 30 during the sampling operation are re-infused by depressing the plunger 64. It should be noted that the pressure transducer 38 may include a flow restrictor or flow control means to prevent flushed solution from going proximally through the sensor rather than back to the patient. For instance, the stopcock 36 may be used to close off the fluid path through the pressure transducer 38 prior to re-infusing the reservoir clearance volume.

The entire sampling system 20 is thus closed as the "priming" volume that ensures a pure sample of blood reaches the sampling site 60 remains within the system 20 and is reinfused into the patient. It will be understood by those skilled in the art that the syringe-type reservoir 30 shown in FIGS. 1-2 is only exemplary and other configurations may be designed to adequately provide the variable volume chamber.

With reference now to FIGS. 3A-3C and 4-5, the proximate relationship between the reservoir 30 and the control valve 32 will be described. Desirably, the reservoir 30 and control valve 32 are molded plastic pieces that are rigidly mounted together such as with adhesive or ultrasonic welding. However, the reservoir 30 simply needs to be in proximity with the control valve 32 such that they are connected by two fluid flow paths. For convention, the ordinary flow path of the whole system as seen in FIG. 1 is from proximal to distal, or from the fluid bag 44 to the patient P. With reference back to FIG. 2, the saline or other physiological fluid flows into the reservoir 30 and control valve 32 combination through the proximal segment 24 of the conduit line and flows out of the distal segment 22. In this regard, therefore, the reservoir 30 has an inlet that receives saline from an outlet port of the control valve 32, and also an outlet through which saline flows to an inlet port of the control valve. These internal flow paths and channels will become clearer below, and as mentioned are desirably molded into the mating sections of the reservoir 30 and control valve 32. It is entirely feasible, however, to separate these two components with short lengths of tubing.

The control valve 32 as best seen in FIGS. 4-5 comprises a manifold 70 that receives a movable valve member 72. In the exemplary embodiment, the manifold 70 defines a cylindrical interior chamber 74 sized to rotatably receive a generally cylindrical core 76 of the valve member 72. A control handle 78 extends externally from the chamber 74 and provides leverage for rotating the core 76 within the chamber. The interior chamber 74 is shown oriented 90° from the axis of the reservoir 30, although other arrangements are possible.

FIGS. 4 and 5 further illustrate an exemplary fluid sampling port 84 provided in an outer portion of the control handle 78. The fluid sampling 44 may take a variety of forms, but as illustrated includes an elastomeric slit septum 86 captured by a cap 88 over a sampling cavity 90 within the valve member 72. The assembly seen in FIG. 4 provides access for a blunt cannula through the slit septum 86 to withdraw fluid from within the sampling cavity 90. The sampling site 84 is located along the center line of the rotating valve member 72, although as will be explained below, other locations for a sampling site within the control valve are contemplated.

FIGS. 4 and 5 also illustrate exemplary indicators for the various rotational positions of the valve member 72 within the manifold 70. More specifically, the preferred form of the invention includes both tactile and visual indicators to help reduce clinician errors, speed up and clarify the process. The visual indicators include an arrow-shaped control handle 78 with a pointed end 92 that registers with one of three symbols 94a, 94b, 94c raised and/or printed on a faceplate 96 of the control valve 32. The valve member 72 may be rotated to one of the three positions with the pointed end 92 registering with one of the three symbols 94a, 94b, 94c. The indicator plate 96 shows the three position indicators 94 at the 0°, 90°, and 180° locations relative to a 0° horizontal reference line to the right (3:00). The 90° angular separation between the positions of the valve member 72 facilitates selection of one of three modes. An arc-shaped lip 98 projecting from an outer end of the interior chamber body desirably interferes with a small tooth 99 (see FIG. 6A) on the valve member 72 to prevent its rotation into the fourth, unmarked quadrant. The meaning of the symbols 94a, 94b, 94c will become apparent below. 91 psuedo inlet/outlet port, good flushing In addition to visual indicators, the control valve 32 also desirably provides tactile feedback to the operator when the valve member 72 is in one of the three discrete positions. There are a number of ways to indicate tactilely the proper positioning of a rotating body within another, but the means used in the present context also preferably provide positive positioning of the valve member 72 within the interior chamber 74. For example, a small rib or bump 100 extending inward from the chamber 74 or lip 78 may be sized in position to register with small grooves or depressions 102 formed in the valve member core 76. These mating features are preferably sized large enough for the male portion to fit within the female portion and nominally restrain motion of the valve member 72, but small enough to allow the user to relatively easily overcome their engagement and further rotate the valve member. As the engaging pieces are molded plastic, and the assembly is designed to be used once and disposed of, small rounded bumps engaging equal sized depressions are an effective short-term tactile indicator. It should be understood that the bumps and depressions could be provided on the parts as shown, or on the opposite elements in a reverse configuration. Moreover, these physical mating features desirably emit a small click when engaging, which provides a third, aural indicator.

FIGS. 6A-6E and 7-11 provide details of the exemplary valve member 72 having the central sampling port 84 therein. With reference to FIG. 6A, the core 76 has a generally cylindrical exterior that slightly narrows away from the control handle 78 and is interrupted at a lower end by a trough 110 bordered by two shoulders 112. A pair of channels 114, 116 through the interior of the core 76 open to the core exterior at two locations separated circumferentially by almost 90° but in a common radial plane (as used herein, "radial" is relative to the rotational axis of the valve member 72). Looking at the reverse orientation of FIG. 6E, the core 76 further features an arc-shaped groove or channel 120 that extends around the circumference of the core in a radial plane, preferably the same plane as that of the openings of the channels 114, 116. FIG. 9 is a radial sectional view through that common plane and illustrates the relative positions and orientations of the channels 114, 116, 120.

The generally cylindrical portion of the core 76 is sized to closely fit within the interior chamber 74 of the manifold 70 (see FIG. 5) such that the valve member 72 can rotate within the manifold but there is no unintended fluid leakage between the various ports and channels. The openings of the channels 14, 16 and the circumferential channel 120 lying in a common radial plane provide the only avenue for fluid passage around or through the valve member 72 when it is closely fit within the interior chamber 74. It should be understood that alternative configurations are possible with, for example, the openings to the channels 114, 116 and circumferential channel 120 being spaced apart axially with respect to one or the others.

FIG. 7 is an axial cross-sectional view through the valve member 72 that illustrates the inner components of the sampling port 84. Namely, the cap 88 restrains the elastomeric slit septum 86 over the sampling cavity 90. FIG. 8 illustrates the sampling cavity 90 along a different axial plane that passes directly between a pair of axially-oriented channels 130, 132 seen in FIG. 7 that communicate, respectively, with the radial channels 114, 116. FIG. 8 further illustrates the generally semi-circular cross-section of the circumferential channel 120. With reference again to FIG. 9, it should therefore be apparent that the radial channels 114, 116 are in constant fluid communication with each other via the respective connecting channels 130, 132 opening into the common sampling cavity 90. As will be explained below, these bifurcated channels through the valve member 72 function to permit blood or other body fluid into the sampling cavity 90, and also effectively flush the sampling cavity 90 in between samples. An axial extension 134 of the wall separating the connecting channels 130, 132 continues into close proximity with the slit septum 86. The extension 134 creates a pseudo inlet/outlet to the sampling cavity 90 such that a flow of flushing fluid therethrough is directed all the way to the slit septum 86 before turning the corner and continuing through the valve member 72. The extension 134 therefore enhances the efficacy of the flushing step and helps eliminate dead zones within the simply cavity 90 that might otherwise be a source of blood coagulation and contamination.

Structural details of the manifold 70 are seen in FIGS. 12-15. Specifically, the manifold 70 features a plurality of ports that opened into the interior chamber 74. A distal port 140 and a proximal port 142 extend upward from the chamber 74 in the orientation where the reservoir 30 plunger points downward. These ports 140, 142 are shown respectively connected to the distal segment 22 and proximal segment 24 of the conduit line in FIGS. 1 and 2. Therefore these ports 140, 142 represent the two diverging segments of the conduit line, the former extending toward the patient and the latter to the pressure transducer 38 and saline drip.

On the opposite side of the chamber 74, a manifold outlet port 144 leads to an inlet 146 to the reservoir variable volume chamber 62. An outlet 148 of the reservoir 30 leads directly into a manifold inlet port 150. The distal and proximal ports 140, 142 and outlet and inlet ports 144, 150 all open directly to the interior chamber 74 of the manifold 70. Note that one possible configuration is a reservoir connected through the control valve 32 using only a single reservoir port as opposed to inlet and outlet ports. For example, a syringe-type removable reservoir may be connected to a single port of the control valve 32. In such a system, the benefit of isolating the reservoir remains although the flush mode of operation will not pass through the reservoir. The term "reservoir port" therefore includes one or both of the outlet and inlet ports 144, 150.

FIGS. 13-14 show the manifold 70 having relatively long outlet and inlet ports 144, 150 leading to and from the reservoir 30 to provide some clearance for rotation of the valve member 72. Desirably, the manifold 70 is a single molded piece that is rigidly secured to the end of the reservoir 30. However, the manifold 70 could be a combination of more than one piece, and could be connected to the reservoir 30 through short tubes.

FIGS. 15A and 15B show the gradual taper of the interior chamber 74 at the narrow end of the chamber 74, a circular rib 160 projects inward for engaging and retaining the valve member 72, as will be explained next.

Figure 16:
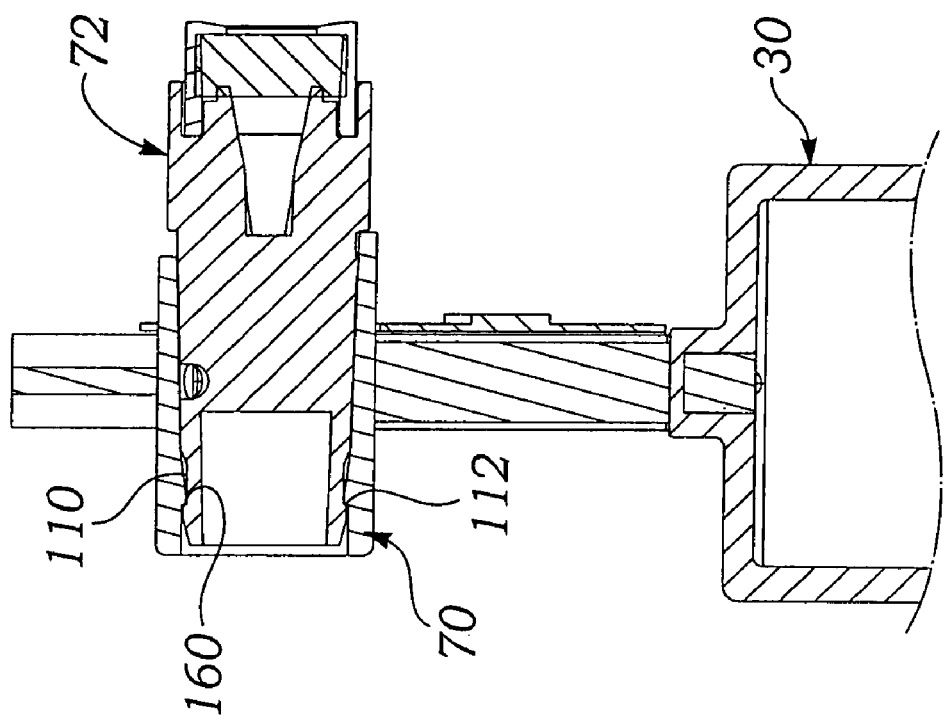
FIGS. 16 and 17 are axial sectional views of the control valve of the present invention taken along lines 16-16 and 17-17, respectively, of FIG. 4.
Figure 17:
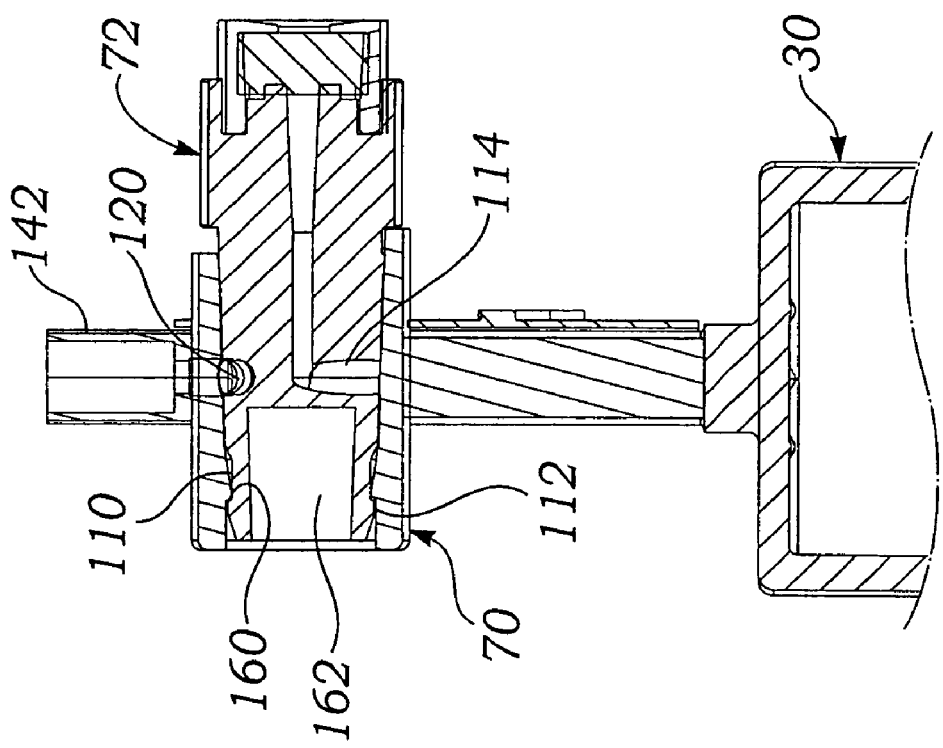

FIGS. 16 and 17 illustrate in cross-section the coupling of the valve member 72 within the manifold 70. Specifically, the gradual tapers of both closely match and provide an effective fluid seal at the point that the inward rib 160 of the manifold passes over the first shoulder 112 of the valve member 72 and resides within the trough 110. A cavity 162 in the narrow end of the valve member 72 permits inward flexing of the shoulder 112 such that it can be forced passed the rib 160. Interference between the outwardly-sprung shoulder 112 and rib 160 effectively locks the valve member 72 within the manifold 70 and ensures good fluid sealing around the various ports and openings. FIG. 16 shows the alignment of the proximal port 142 with the circumferential groove 120 two valve member 72. Likewise, the radial channel 114 also lies in the same plane. It is worth mentioning again at this stage that the coplanar nature of all of the ports and openings is an efficient and relatively straightforward design, but more complex fluid pathways between the rotating valve member 72 and manifold 70 could be designed to perform the same function. For example, one or more of the internal channels could be curvilinear, or there could be more than one circumferential surface channel.

Now with reference to FIGS. 18A-18C and 19A-1C, the fluid flow paths for the three positions of the valve member 72 will be explained.

The reader will recall from the description of the system of FIG. 1 that there is a physiological fluid flush drip, preferably pressurized. When such flush is needed, the clinician rotates the valve member 72 to the downward position, as indicated by the arrow F/C in FIG. 18A. This corresponds to a "Flush/Clear" mode of operation, and is symbolically indicated by the symbol 94a of three divergent flow paths in FIG. 5, meaning all fluid communications are open. When pressure monitoring is desirable, the clinician rotates the valve member 72 to the left position, as indicated by the arrow M in FIG. 18B. This corresponds to a "Monitoring" mode of operation, and is symbolically indicated by the symbol 94b of a pressure wave in FIG. 5. Finally, when the clinician requires a fluid sample, he/she rotates the valve member 72 to the right position, as indicated by the arrow S in FIG. 18C. This corresponds to a "Sampling" mode of operation, and is symbolically indicated by the symbol 94C of a drop of fluid in FIG. 5. As mentioned above, the symbolic indicators 94a, 94b, and 94c are desirably supplemented by the clear directional nature of the arrow-shaped control handle 78, and by tactile and audible feedback measures, to help avoid error.

FIGS. 18A-18C further illustrate the change in rotational orientation of the valve member 72 within the internal chamber of the manifold 70, in particular through the radial plane passing through the flow channels that open to the exterior of the valve member core 76. The same illustrations of the flow channels in the three positions are shown more clearly in FIGS. 19A-19C with relevant labels and fluid flows indicated. The two sets of diagrams further indicate the four manifold ports 140, 142, 144, and 150.

In the F/C position of the valve member 72 of FIGS. 18A and 19A, a slow drip of flushing fluid travels from the supply of flush solution 44 (FIG. 1) through the proximal segment 24 (FIG. 2) to the manifold proximal port 142, through the circumferential channel 120 and the outlet port 144. As indicated by the flow arrows in FIG. 19A, the drip continues through the inlet 146 and outlet 148 of the reservoir 30 passing through the variable volume chamber 62. The fluid then passes through the inlet port 150 into the radial channel 114, and along the axial channel 130 into the sampling reservoir 90 (see FIG. 7), and back through the parallel axial channel 132 into the other radial channel 132. Finally, the fluid exits the valve member 72 into the manifold distal port 140 and from there continues through the distal segment 22 of the conduit line to the patient.

In the F/C position of the valve member 72, all of the internal flow paths within the reservoir 30 and control valve 32 are open to form a single continuous flushing pathway. This desirably permits any blood or other bodily fluid to be completely flushed from within the system 20, leaving no dead spots for bubbles to form or blood to coagulate. This "pocket-less" fluid pathway through the system in conjunction with the ability to isolate components that degrade the pressure signal is extremely useful. Furthermore, the control valve 32 is desirably made of transparent or frosted plastic that permits the user to visualize blood flow therethrough, thus insuring blood as been completely flushed out of the system after a sample is taken.

The F/C position also enables a clearing volume to be pulled into the reservoir 30. Specifically, a reduced pressure within the variable volume chamber 62 pulls fluid from the distal segment 22 into the reservoir 30 in a reverse flow from that shown in FIG. 19A. The volume of the chamber 62 is sufficient to draw blood from the patient past the sampling port 84 (sampling cavity 90), that is, through the internal channels of the valve member 72. A flow restrictor or control valve at the pressure transducer 38 toward the proximal segment 24 ensures that the reservoir 30 fills with fluid from the distal segment 22. That is, there is greater resistance to flow into the reservoir from the proximal segment 24 as compared to the distal segment 22.

Before a sample is taken, however, the control handle 78 must be rotated into the third S position shown in FIGS. 18C and 19C. In this position, the channels of the valve member 72 provide open fluid communication only from the distal port 140 to the radial channel 114 as shown, and from there to the sampling cavity 90 (FIG. 7). A fluid sample is taken from the port 84 using a blunt cannula or other sampling device.

Pressure monitoring occurs with the valve member 72 in the second M position shown in FIGS. 18B and 19B. In that position, the pressure transducer 38 (or DPT, Disposable Pressure Transducer), is in fluid communication with the patient directly though the circumferential channel 120, bypassing the reservoir 30 and sampling port 84. This feature of the control valve 32 isolates the elastomeric elements of the reservoir 30 and sampling port 84, as well as the associated channels leading thereto, from the fluid pressure column. The fluid pressure column therefore extends directly from the patient through the distal segment 22, making a U-turn in the circumferential channel 120 to the proximal segment 24. Bypassing the reservoir 30, and in particular the elastomeric seal of the plunger 64, and the sampling port 84 (elastomeric septum 86), greatly improves the signals received by the pressure transducer 38. A distal sampling port 60 in the distal segment 22 may be of a conventional type which includes an elastomeric septum that would affect the pressure signal, or that sampling port may also be isolated from the pressure column as will be described below. One benefit of improving the pressure response of the system by isolating the various functional elements is that the entire conduit line can be lengthened to move the reservoir 30 farther away from the patient. In conventional blood sampling systems, where the elastomeric components remain in contact with the pressure column, the maximum length of the conduit line from the reservoir to the patient is about _ cm. By isolating just the reservoir 30 as indicated above, the conduit line can be lengthened to about _ cm. [Mark, please fill in these distances]

It is important to understand that the principles of the control valve 32 described above are applicable to other configurations of fluid sampling systems. In the exemplary system described above, a sampling port 84 is incorporated centrally in the rotating valve member 72 of the control valve 32, which is connected or adjacent to the reservoir 30. The control valve 32 isolates both the reservoir and the sampling port in the sampling mode. However, the sampling port in the control valve may connect through the manifold 70 instead of the valve member 72. Also, the exemplary valve member has three positions 90° apart from each other, but the arrangement of the channels within the valve member and manifold may be altered to change the amount of the valve member rotates in each position. Furthermore, the principles of isolating the elastomeric elements of the reservoir and sampling port can be transferred to a stand-along sampling port in the conduit line. Examples of each of these alternatives will be described below, and it should be clear that these are representative of numerous other alternatives.

FIGS. 20A-20E illustrate an alternative control valve 170 of the present invention adjacent a reservoir 30 with a modified arrangement of internal flow paths than the exemplary embodiment described above. The control valve 170 is similar to the first embodiment in that a housing or manifold 172 connects to the reservoir 30 and rotatably receives therein a valve member 174. Furthermore, the valve member 174 carries a central sampling port 176, which is illustrated as a slit septum-type but could be any number of kinds of sampling ports. FIG. 20B shows a control handle 178 of the valve member 174 oriented with its pointed and 180 down into the right at about a 45° angle. The indicator plate 182 shows the three position indicators at the 45°, 90°, and 180° locations relative to a horizontal reference line to the right at 0°. This is a departure from the 90° separation between the valve member positions in the first embodiment.

The control handle 178 in FIG. 20B is in the "S" or sampling position. The internal flow channels defined within the valve member 174 in the radial plane of the ports of the manifold 172 are illustrated in FIG. 20E. Comparing this view with a similar view shown in FIG. 18C, the reader will discern the slightly different orientations of the internal channels within the valve member 174. By rotating the valve member 174 clockwise another 45°, the control valve 170 will be placed in the F/C mode wherein all of the internal flow paths are in series so that the system can be flushed. Rotating the valve member 174 a further 90° into the M position isolates both the reservoir 30 and the sampling port 176 from the attached conduit line for undegraded pressure monitoring. Although the relative spacing between the S position and the F/C position is only 45°, in contrast with 90° in the first embodiment, the flow channels are modified to prevent crosstalk or pressure perturbations transmitted to the proximal segment and pressure transducer when switching positions. Furthermore, the channels are arranged so that there is greater separation between the internal channels in the sampling mode.

FIGS. 21A-21E show another alternative control valve 190 similar to the valve 170 of FIG. 20A-20E, but with a luer-style central sampling port. Specifically, the control valve 190 includes the modified internal flow paths such that the three operating positions of a control handle 192 seen in FIG. 21B are other than 90° apart. More particularly, the cross-section of FIG. 21E is the same as that of FIG. 20E. Also, the control valve 190 includes a sampling port 194 provided in the center of a rotatable valve member 196. In contrast to the embodiments of FIGS. 20A-20E, however, the sampling port 194 includes a luer-style connector 198, best seen in FIG. 21C. The male luer-style connector 198 mates with a female luer connector on a sampling syringe (not shown). Because of the typically larger sizes of the blunt cannulas in such sampling syringes, the septum 200 of the sampling port 194 is highly compliant, or at least more compliant than the slit septum 86 used in the sampling port 84 described above. The ability to isolate the luer-style sampling port 194 using the control valve 190 is therefore highly desirable as it greatly improves the quality of the pressure signal received by the pressure transducer by removing the compliance of the septum 200 from the pressure column.

FIGS. 22A-22E illustrates a control valve 210 that, as before, may be associated with or connected to a reservoir 30, but includes an alternative fluid sampling port 212. Specifically, the fluid sampling port 212 comprises a side port from a control valve manifold 214 rather than being formed centrally in a rotatable valve member 216. The sampling port 212 is shown in cross-section in FIG. 22E which reveals an elastomeric septum 220 captured by a cap 222 over a sampling cavity 224. A pair of flow channels 226, 228 open into the sampling cavity 224. The opposite ends of the flow channels 226, 228 opened to an interior chamber of the control valve manifold 214. In this sense, the sampling port 212 communicates with internal channels in the control valve 210 via a through flow path defined by the channels 226, 228.

Figure 22D:
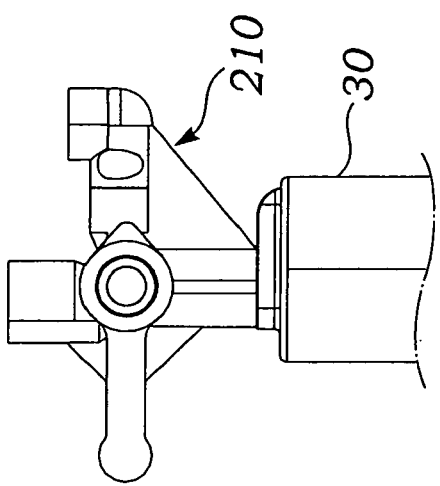
FIGS. 22A-22E are various external and sectional views of an alternative control valve with a sampling port extending from the side of a manifold.
Figure 22A:
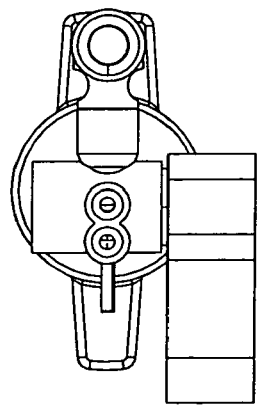
Figure 22B:
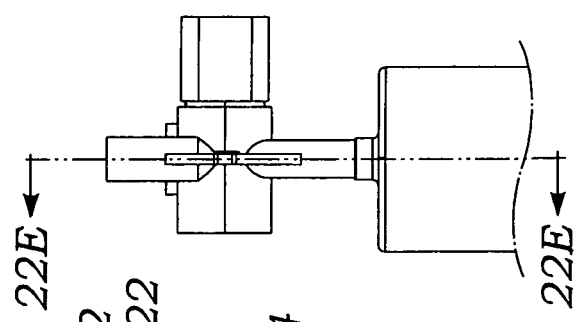
Figure 22E:
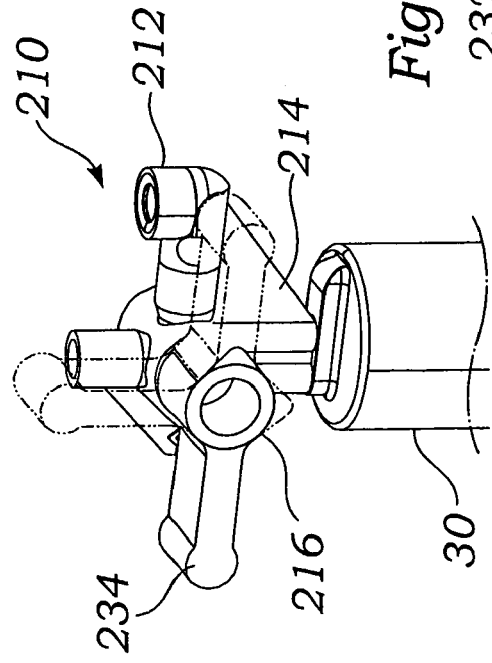
Figure 22C:
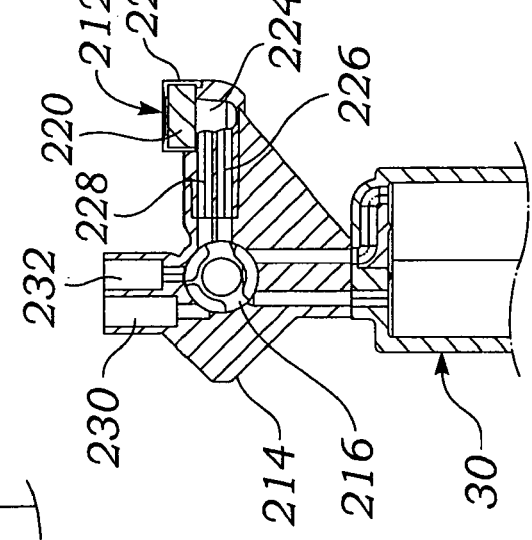

FIG. 22E also shows six openings to the internal channel of the manifold 214, two of which lead to the sampling port channels 226, 228. Another two openings lead to proximal and distal ports 230, 232 that connect to the proximal and distal conduit line segments. Finally, two more openings lead respectively to the inlet and outlet of the reservoir 30. The valve member 216 includes circumferential channels that selectively communicate with these 6 ports depending on the rotational position of a handle 234. As with the earlier embodiments, there are 3 positions of flush, monitor, and sample. In the monitor position, the control valve 210 isolates both the reservoir 30 and sampling port 212 from the conduit line for a more accurate pressure signal. Also, the valve 210 prevents flow from the proximal conduit line segment in the sampling mode. This embodiment illustrates the alternative of having the sampling port connected with the control valve manifold as opposed to the rotating valve member.

FIGS. 23A-23E are various views of a luer-style valved sampling station 250 which can be incorporated into a pressure monitoring line in conjunction with a reservoir or independently. The valved sampling station 250 includes a housing or manifold 252 that defines therewithin an internal chamber 254 as seen in FIG. 24 with which a pair of ports 256, 258 communicate. The downstream port 256 may be connected to the patient, while an upstream port 258 is connected to a pressure transducer (not shown), in like manner as the manifold ports 140, 142 seen in FIG. 12. Additionally, a loop-shaped channel 260 formed in the manifold 252 has opposite ends that open to the internal chamber 254. A valve member 262 rotates within the internal chamber 254. The valve member 262 has the same configuration has the valve member 196 shown in FIGS. 21A-21E. That is, the internal flow channels are the same and the valve member 262 carries a central luer-type sampling port 264.

With reference to FIG. 23B, the manifold 252 includes an indicator plate 266 on which are provided the familiar three operational mode symbols of sampling, flush, and pressure monitoring. A control handle 268 is used to rotate the valve member 262 into the three operational positions. The reader will recognize that the three positions have the same spacing as the positions for the control valve 190 in FIGS. 21A-21E. Indeed, the valved sampling station 250 functions analogously to the control valve 190 in that in the pressure monitoring position of the control handle 268, the central sampling port 264 is isolated from the ports 256, 258, and thus the attached conduit line and pressure column. The sole difference between the valved sampling station 250 and the control valve 190 is the substitution of the loop-shaped channel 260 for the clearance reservoir. The channel 260 is important in that a flow of fluid passes through it and through all of the internal channels of the valved sampling station 250 when the control handle 268 is in the flush position, seen in FIG. 23B. Again, the valved sampling station 250 can be used in a conduit line of a pressure monitoring system where a clearance volume of fluid is pulled past the sampling port using a reservoir as described above, or other such clearing device.

Finally, FIGS. 25A-25E illustrate a further alternative valved sampling station 280 with a sampling port 282 extending from one side of a manifold 284. The manifold 284 is configured in a T-shape with a pair of ports 286, 288 that open to an internal chamber projecting outward at 90° with respect to one another, and with respect to the sampling port 282. The valve member 290 rotates within the internal chamber. As seen in FIG. 25E, the valve member 290 includes two circumferential channels 292, 294 that selectively communicate with the ports 286, 288, and with two ports 296, 298 leading to and from the sampling port 282. As in the valved sampling station 250 of FIGS. 23-24, the valve member 290 rotates into three positions corresponding to flush, sampling, and pressure monitoring. The ports 286, 288 attach to proximal and distal segments of a conduit line in a manner described above. In the pressure monitoring mode, the sampling station 280 excludes the sampling port 282 from the conduit line. This embodiment is similar to the immediately preceding sampling station 250, but illustrates a sampling port 282 that connects directly to the manifold 284 rather than to the rotating valve member 290. Furthermore, the sampling port 282 has a slit septum 299 for receiving a blunt cannula (not shown), but a luer-type sampling port could also be used.

While the invention has been described in its preferred embodiments, it is to be understood that the words which have been used are words of description and not of limitation. Therefore, changes may be made within the appended claims without departing from the true scope of the invention.

What is claimed is:

1. A medical system for fluid sampling and pressure monitoring of a fluid system of a patient, comprising:
   a conduit line with a proximal segment adapted to be supplied with a physiological fluid and a distal segment adapted to be in communication with a fluid system of a patient;
   a control valve with a manifold defining an interior chamber, the manifold having a proximal port fluidly connected to the proximal segment, a distal port fluidly connected to the distal segment, and at least one reservoir port, wherein each of the manifold ports opens to the interior chamber,
   a pressure transducer connected to the conduit line for sensing the pressure of the fluid therein;
   a fluid sampling port in the medical system;
   a reservoir in fluid communication with the at least one reservoir port of the control valve manifold;
   the control valve further including a valve member movable within the interior chamber and having a plurality of channels therein that selectively communicate with the manifold ports, wherein the plurality of channels comprises a first fluid path and a second fluid path, wherein the first fluid path is separate from the second fluid path, the valve member being movable into at least two positions:
      a first position that provides open fluid communication from the proximal segment to the patient through the control valve so as to eliminate any dead spaces therein, wherein the first fluid path provides an open fluid passage from the proximal port to one of the at least one reservoir ports, wherein the second fluid path provides an open fluid passage from the distal port to one of the at least one reservoir ports, and wherein reduced pressure within the reservoir pulls fluid from the distal segment through the control valve and into the reservoir sufficient to draw fluid from the fluid system of the patient past the sampling port, and a second position that provides open fluid communication from the proximal segment to the proximal port and through the first fluid path in the valve member to the distal segment, and wherein the proximal segment and distal segment are not in fluid contact with the reservoir and second fluid path and sampling port, such that the pressure of fluid within the conduit line exclusive of the reservoir can be sensed by the pressure transducer.

2. The system of claim 1, wherein the valve member has a third position that provides open fluid communication from the distal segment to the sampling port via the second fluid path but prevents communication between the sampling port and both the reservoir and the proximal segment.

3. The system of claim 1, wherein the valve member comprises a core rotatable within the interior chamber of the manifold and a control handle external to the manifold, further including coordinated visible features on the control handle and manifold that provide symbolic indicators of both first and second positions of the valve member.

4. The system of claim 1, wherein the sampling port is formed within the control valve.

5. The system of claim 4, wherein the sampling port is formed within the valve member and communicates with a sampling cavity formed internally within the valve member and open to the second fluid path of the valve member.

6. The system of claim 4, further including a second sampling port having a sampling cavity positioned along the distal segment of the conduit line.

7. The system of claim 6, further including a second control valve interposed between the second sampling port and the distal segment and having a valve member movable into at least three positions:
a first position that provides open fluid communication from the conduit line through the control valve to the sampling cavity and back to the conduit line,
a second position that provides open fluid communication from the conduit line through the valve member and back to the conduit line while bypassing the second sampling port, such that the pressure of fluid within the conduit line exclusive of the second sampling port can be sensed by the pressure transducer, and
a third position that provides open fluid communication from the distal segment through the control valve to the second sampling port but prevents communication between the second sampling port and the conduit line proximal from the second sampling port.

8. The system of claim 1, wherein the valve member comprises a core movable within the interior chamber of the manifold and a control handle external to the manifold, the core having an external channel formed along an exterior surface of the core and an internal channel formed along an interior bore of the core.

9. The system of claim 8, wherein the internal channel opens to the exterior surface of the core at two separated locations spaced from the external channel.

10. The system of claim 1, further including means for pressurizing the physiological fluid such that at least some fluid continues to flow through the conduit line to the patient when the valve member is in the first position.

11. The system of claim 1, wherein the manifold comprises at least two reservoir ports, wherein a first of the at least two reservoir ports is a reservoir outlet port and a second of the at least two reservoir ports is a reservoir inlet port, wherein the reservoir has an inlet open to the reservoir outlet port of the control valve manifold and an outlet open to the reservoir inlet port of the control valve manifold, and wherein the first position of the valve member provides open fluid communication between the control valve flow passages through the inlet and outlet of the reservoir to flush a chamber of the reservoir.

12. A medical system for fluid sampling of a fluid system of a patient, comprising:
a conduit line with a proximal segment adapted to be supplied with a physiological fluid and a distal segment adapted to be in communication with a fluid system of a patient;
a control valve connected between the proximal segment and the distal segment of the conduit line;
a fluid sampling port having a flow path therethrough whose opposite ends open to internal channels in the control valve;
a reservoir in fluid communication with a reservoir port of the control valve manifold;
the control valve further including a valve member movable into at least three positions:
a first position that provides open fluid communication from the proximal segment through the reservoir to the distal segment, wherein at least some fluid from the proximal segment must pass through the reservoir to reach the distal segment,
a second position that provides open fluid communication from the proximal segment to the distal segment while bypassing the reservoir and sampling port, and
a third position that provides open fluid communication from the distal segment to the sampling port but prevents communication between the sampling port and both the reservoir and the proximal segment.

13. The system of claim 12, wherein:
the control valve further includes a manifold defining an interior chamber, the manifold having a proximal port fluidly connected to the proximal segment of the conduit line, a distal port fluidly connected to the distal segment, an outlet port, and an inlet port, wherein each of the manifold ports opens to the interior chamber, and wherein the valve member comprises a core movable within the interior chamber of the manifold and having channels therein that selectively communicate with the manifold ports, and the reservoir has an inlet open to the manifold outlet port and an outlet open to the manifold inlet port, and wherein:
the first position provides open fluid communication from the proximal segment to the proximal port and the outlet port of the control valve, through the inlet and outlet of the reservoir, to the inlet port and the distal port of the control valve to the distal segment,
the second position provides open fluid communication from the proximal segment to the proximal port and through at least one channel in the valve member core to the distal segment while bypassing the reservoir and sampling port, and
the third position provides open fluid communication from the distal segment to distal port and one of the channels of the valve member core, and to the sampling port.

14. The system of claim 13, wherein the valve member core has an external channel formed along an exterior surface of the core and an internal channel formed along an interior bore of the core.

15. The system of claim 14, wherein the internal channel opens to the exterior surface of the core at two separated locations spaced from the external channel.

16. The system of claim 12, wherein the control valve further includes a manifold defining an interior chamber in which the valve member moves, and wherein the sampling port is formed within the valve member and includes a sampling cavity open to channels within the valve member that communicate with the manifold interior chamber.

17. The system of claim 12, wherein the control valve further includes a manifold defining an interior chamber and the valve member comprises a movable within the interior chamber of the manifold and a control handle external to the manifold, and further including coordinated visible features on the control handle and manifold that provide symbolic indicators of all three positions of the valve member.

18. A method of taking samples and measuring the pressure of a fluid system of a patient, comprising:
   providing a fluid sampling system with a conduit line and a reservoir connected thereto between a proximal segment adapted to be supplied with a physiological fluid and a distal segment adapted to be in communication with a fluid system of a patient;
   interposing a control valve between the reservoir and the conduit line having a movable valve member with a control handle, the valve member movable into at least a first position and a second position;
   providing a pressure transducer connected to the conduit line for sensing the pressure of the fluid therein;
   providing a fluid sampling port in the sampling system;
   selecting the first position of the valve member to provide open fluid communication from the proximal segment to the distal segment via the control valve and the reservoir, and creating a reduced pressure within the reservoir such that fluid flows from the distal segment through the control valve into the reservoir sufficient to draw fluid from the fluid system of the patient past the sampling port; and
   selecting the second position of the valve member to provide open fluid communication from the proximal segment to the distal segment via the control valve while bypassing the reservoir, and monitoring the pressure sensed by the pressure transducer.

19. The method of claim 18, wherein the valve member has a third position, and the method includes selecting the third position of the valve member to provide open fluid communication from the distal segment to the sampling port but prevent communication between the sampling port and both the reservoir and the proximal segment, and sampling fluid from the conduit line through the sampling port.

20. The method of claim 19, wherein the fluid system of the patient is the blood system, and further including means for pressurizing the physiological fluid such that at least some fluid continues to flow through the conduit line to the patient when the valve member is in the first position, the method including the steps of:
   selecting the first position of the valve member such that the physiological fluid flows through the conduit line to the patient; then creating a reduced pressure within reservoir and collecting sufficient fluid therein such that blood flows past the sampling port; then
   selecting the third position of the valve member; then
   sampling blood from the conduit line through the sampling port; then
   creating an elevated pressure within the reservoir to expel blood therefrom into the distal segment of the conduit line; then
   selecting the first position of the valve member such that the physiological fluid flows through the conduit line to the patient and flushes the reservoir of blood; and then
   selecting the second position of the valve member and monitoring the pressure sensed by the pressure transducer.

21. The method of claim 18, wherein the control valve includes visible features that provide symbolic indicators of the first and second positions of the control handle, the method of selecting the first and second positions further includes interpreting the symbolic indicators to determine the placement of the control handle corresponding to the first and second positions.

22. A medical system for fluid sampling of a fluid system of a patient, comprising:
   a conduit line with a proximal end adapted to be supplied with a physiological fluid and a distal end adapted to be in communication with a fluid system of a patient;
   a pressure transducer connected to the conduit line for sensing the pressure of the fluid therein;
   a fluid sampling port having a sampling cavity;
   a control valve interposed between the conduit line and the sampling port and having a manifold defining an interior chamber, the manifold having a proximal port fluidly connected to the conduit line, a distal port fluidly connected to the conduit line, an outlet port, and an inlet port, wherein each of the manifold ports opens to the interior chamber,
   the control valve further including a valve member movable within the interior chamber and having channels therein that selectively communicate with the manifold ports, the valve member being movable into at least three positions:
      a first position that provides a first path of open fluid communication from the conduit line to the proximal port and the outlet port of the control valve, and a second path of open fluid communication from the inlet port and the distal port of the control valve to the conduit line via the sampling cavity, wherein the first path is separate from the second path of open fluid communication,
      a second position that provides open fluid communication from the conduit line to the proximal port and through at least one channel in the valve member and back to the conduit line while bypassing the sampling port, such that the pressure of fluid within the conduit line exclusive of the sampling port can be sensed by the pressure transducer, and
      a third position that provides open fluid communication from the distal end of the conduit line through the control valve to the sampling port but prevents communication between the sampling port and the proximal end of the conduit line.

23. The system of claim 22, wherein the valve member comprises a core movable within the interior chamber of the manifold and having an external channel formed along an exterior surface of the core and an internal channel formed along an interior bore of the core.

24. The system of claim 23, wherein the internal channel opens to the exterior surface of the core at two separated locations spaced from the external channel.

25. The system of claim 22, wherein the sampling port is formed within the valve member and the sampling cavity is open to the valve member channels.

26. The system of claim 22, wherein the valve member comprises a core movable within the interior chamber of the manifold and a control handle external to the manifold.

27. The system of claim 26, further including coordinated visible features on the control handle and manifold that provide symbolic indicators of all three positions of the valve member.

* * * * *